(12) United States Patent
Choi et al.

(10) Patent No.: US 9,028,144 B2
(45) Date of Patent: May 12, 2015

(54) X-RAY IMAGING APPARATUS AND METHOD FOR CONTROLLING THE SAME

(71) Applicant: Samsung Electronics Co., Ltd., Suwon-si (KR)

(72) Inventors: Choong Hwan Choi, Suwon-si (KR); Do Kwan Oh, Suwon-si (KR); Woo Sup Han, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 13/919,496

(22) Filed: Jun. 17, 2013

(65) Prior Publication Data

US 2014/0153697 A1 Jun. 5, 2014

(30) Foreign Application Priority Data

Dec. 5, 2012 (KR) ........................ 10-2012-0140002

(51) Int. Cl.
*A61B 6/08* (2006.01)
*H05G 1/26* (2006.01)
*G01N 23/083* (2006.01)
*A61B 6/00* (2006.01)
(Continued)

(52) U.S. Cl.
CPC . *A61B 6/54* (2013.01); *A61B 6/032* (2013.01); *A61B 6/0407* (2013.01); *A61B 6/08* (2013.01); *A61B 6/4233* (2013.01); *A61B 6/4464* (2013.01); *A61B 6/467* (2013.01); *G06F 3/017* (2013.01); *Y10S 378/901* (2013.01)

(58) Field of Classification Search
CPC ..................................... H05G 1/60; A61B 6/08
USPC ............ 378/4, 8, 19, 20, 62, 91, 95, 98, 98.2, 378/193, 195–197, 204, 205, 207–210, 901
See application file for complete search history.

(56) References Cited

U.S. PATENT DOCUMENTS 4,118,631 A * 10/1978 Froggatt .......................... 378/65
6,219,403 B1 * 4/2001 Nishihara ....................... 378/65
(Continued)

FOREIGN PATENT DOCUMENTS

| DE | 195 08 715 A1 | 9/1996 |
| DE | 103 35 037 A1 | 3/2005 |
| WO | 2012129474 A1 | 9/2012 |

OTHER PUBLICATIONS

Communication dated Oct. 31, 2013 issued by the European Patent Office in counterpart European Patent Application No. 13172001.3.

*Primary Examiner* — Anastasia Midkiff
(74) *Attorney, Agent, or Firm* — Sughrue Mion, PLLC

(57) ABSTRACT

Disclosed herein are an X-ray imaging apparatus which recognizes a marker located at a part to be subjected to X-ray imaging from an image of a subject imaged by a camera and which controls a respective movement of each of an X-ray tube and an X-ray detector to a respective position which corresponds to the recognized marker, and a method for controlling the same. An X-ray imaging apparatus includes an X-ray tube which radiates X-rays toward a subject, an X-ray detector which detects X-rays which propagate through the subject, an imaging unit which generates an image of the subject, a recognizer which recognizes a part to be subjected to X-ray imaging from the image of the subject, and a position controller which controls a movement of the X-ray tube and the X-ray detector to a position corresponding to the part to be subjected to X-ray imaging.

32 Claims, 24 Drawing Sheets

(51) Int. Cl.
*A61B 6/03* (2006.01)
*A61B 6/04* (2006.01)
*G06F 3/01* (2006.01)

(56) References Cited

U.S. PATENT DOCUMENTS

| | | | |
|---|---|---|---|
| 6,259,942 B1* | 7/2001 | Westermann et al. | 600/426 |
| 6,585,412 B2* | 7/2003 | Mitschke | 378/207 |
| 6,714,629 B2* | 3/2004 | Vilsmeier | 378/165 |
| 6,859,521 B2 | 2/2005 | Spahn | |
| 7,401,977 B2 | 7/2008 | Graumann et al. | |
| 7,433,503 B2 | 10/2008 | Cherek et al. | |
| 2005/0025706 A1 | 2/2005 | Kagermeier | |
| 2009/0046906 A1 | 2/2009 | Wohlgemuth et al. | |
| 2010/0135467 A1* | 6/2010 | King et al. | 378/163 |
| 2012/0116374 A1 | 5/2012 | Jia et al. | |

* cited by examiner

X-RAY IMAGING APPARATUS AND METHOD FOR CONTROLLING THE SAME

CROSS-REFERENCE TO RELATED APPLICATION

This application claims priority from Korean Patent Application No. 10-2012-0140002, filed on Dec. 5, 2012 in the Korean Intellectual Property Office, the disclosure of which is incorporated herein by reference in its entirety.

BACKGROUND

1. Field

Exemplary embodiments relate to an X-ray imaging apparatus which may be used to control positions of an X-ray tub and an X-ray detector, radiate X-rays toward a subject, and detect X-rays which propagate through the subject, and a method for controlling the same.

2. Description of the Related Art

An X-ray imaging apparatus radiates X-rays toward a subject, analyzes X-rays which propagate through the subject, and checks an internal structure of the subject. Because propagation of X-rays varies based on tissue type, an internal structure of the subject may be imaged by using an attenuation coefficient obtained by digitizing the propagation of the X-rays.

Upon X-ray imaging, an X-ray tub and an X-ray detector are moved based on an imaged part of a subject. Therefore, before X-ray imaging, a user directly controls an X-ray generator and an X-ray detector.

This increases user fatigue and increases an imaging time. Because it is difficult to precisely control the position of the X-ray tube which has a large volume, X-ray imaging is repeated and a patient is exposed to a greater amount of X-ray radiation.

SUMMARY

Therefore, exemplary embodiments disclosed herein provide an X-ray imaging apparatus which recognizes a marker located at a part to be subjected to X-ray imaging from an image of a subject imaged by a camera and which controls a respective movement of each of an X-ray tube and an X-ray detector to a respective position which corresponds to the recognized marker in order to prevent an inconvenience, such as a direct movement of the X-ray tube and the X-ray detector, and in order to reduce an X-ray imaging time and the amount of X-rays to which a patient is exposed, and a method for controlling the same.

Additional aspects will be set forth in part in the description which follows and, in part, will be obvious from the description, or may be learned by practice of the exemplary embodiments.

In accordance with one aspect of one or more exemplary embodiments, there is provided an X-ray imaging apparatus which includes an X-ray tube which radiates X-rays toward a subject, an X-ray detector which detects X-rays which propagate through the subject, an imaging unit which generates an image of the subject, a recognizer which recognizes a part to be subjected to X-ray imaging from the generated image of the subject, and a position controller which controls a respective movement of each of the X-ray tube and the X-ray detector to a respective position which corresponds to the part to be subjected to X-ray imaging.

The recognizer may include a marker recognizer which recognizes a marker from the generated image of the subject in order to recognize the part to be subjected to X-ray imaging of the subject, and the marker may be located at the part to be subjected to X-ray imaging of the subject.

The position controller may control each of a center of an X-ray radiation region of the X-ray tube and a center of an X-ray detection region of the X-ray detector to match with a position of the marker.

The position controller may include a position calculator which calculates the position of the marker, and a control amount calculator which pre-stores information relating to a relative position between the generated image of the subject and at least one of the X-ray tube and the X-ray detector, and which calculates a control amount for causing respective positions of each of the X-ray tube and the X-ray detector to respectively correspond to the calculated position of the marker based on the relative position.

The marker recognizer may recognize at least one of a shape, a color, a material and a size of the marker.

The marker may include an object having a recognizable feature and may include a user's hand having a specific shape.

The marker recognizer may recognize an object having the at least one of the shape, the color, the material, and the size of the marker from the generated image of the subject.

The imaging unit may include a wide-angle camera having an angle of view such that the image of the subject is generated in a single stage.

The imaging unit may be mounted in the X-ray tube, and the position calculator may update a position calculation result of the part to be subjected to X-ray imaging while the X-ray tube moves to the respective position which corresponds to the part to be subjected X-ray imaging.

The recognizer may include an imaged-part recognizer which pre-stores information relating to a feature of the part to be subjected to X-ray imaging and which recognizes the feature from the generated image of the subject.

In accordance with another aspect of one or more exemplary embodiments, there is provided an X-ray imaging apparatus which includes a gantry which includes an X-ray tube which radiates X-rays toward a subject and an X-ray detector which detects X-rays which propagate through the subject, a slider which moves the subject to a bore of the gantry, an imaging unit which generates an image of the subject, a recognizer which recognizes a part to be subjected to X-ray imaging from the generated image of the subject, and a position controller which controls a movement of the slider such that a position of the part to be subjected to X-ray imaging corresponds to a respective position of at least one of the X-ray tube and the X-ray detector.

The recognizer may include a marker recognizer which recognizes a marker from the generated image of the subject in order to recognize the part to be subjected to X-ray imaging, and the marker may be located at the part to be subjected to X-ray imaging.

The position controller may include a position calculator which calculates a position of the marker, and a control amount calculator which pre-stores information relating to a relative position between the generated image of the subject and at least one of the X-ray tube and the X-ray detector, and which calculates a control amount for causing the slider to move based on the pre-stored information relating to the relative position.

The recognizer may include an imaged-part recognizer which pre-stores information relating to a feature of the part to be subjected to X-ray imaging and which recognizes the feature from the generated image of the subject.

In accordance with another aspect of one or more exemplary embodiments, there is provided a method for controlling an X-ray imaging apparatus which includes an X-ray tube which radiates X-rays toward a subject and an X-ray detector which detects X-rays which propagate through the subject, the method including generating an image of the subject, recognizing a part to be subjected to X-ray imaging from the generated image of the subject, and controlling a respective movement of each of the X-ray tube and the X-ray detector to a respective position which corresponds to the part to be subjected to X-ray imaging.

The recognizing the part to be subjected to X-ray imaging may include recognizing a marker from the generated image of the subject in order to recognize the part to be subjected to X-ray imaging of the subject.

The controlling the respective movement of each of the X-ray tube and the X-ray detector to the position which corresponds to the part to be subjected to X-ray imaging may include controlling each of a center of an X-ray radiation region of the X-ray tube and a center of an X-ray detection region of the X-ray detector to match with a position of the marker.

The controlling the respective movement of each of the X-ray tube and the X-ray detector to the position which corresponds to the part to be subjected to X-ray imaging may include pre-storing information relating to a relative position between the generated image of the subject and at least one of the X-ray tube and the X-ray detector, calculating a position of the marker, and calculating a control amount for causing respective positions of each of the X-ray tube and the X-ray detector to respectively correspond to the calculated position of the marker based on the relative position.

The method may further include pre-storing information relating to a feature which includes information relating to at least one of a shape, a color, a material and a size of the marker.

The marker may include an object having a recognizable feature and may include a user's hand having a specific shape.

The recognizing the part to be subjected to X-ray imaging of the subject may include recognizing an object having the feature which includes the information relating to at least one of the shape, the color, the material, and the size of the marker from the generated image of the subject.

The image of the subject may be generated by using a wide-angle camera having an angle of view such that the image of the subject is generated in a single stage.

An imaging unit may be mounted in the X-ray tube, and the calculating the position of the marker may include updating a position calculation result of the part to be subjected to X-ray imaging while the X-ray tube moves to the respective position which corresponds to the part to be subjected X-ray imaging.

The method may further include pre-storing information relating to a feature of the part to be subjected to X-ray imaging, and the recognizing the part to be subjected to X-ray imaging may include recognizing the feature from the generated image of the subject.

In accordance with a further aspect of one or more exemplary embodiments, there is provided a method for controlling an X-ray imaging apparatus which includes a gantry which includes an X-ray tube which radiates X-rays toward a subject and an X-ray detector which detects X-rays which propagate through the subject, the method including moving a slider, on which the subject is located, to a bore of the gantry, generating an image of the subject, recognizing a part to be subjected to X-ray imaging from the generated image of the subject, and controlling a movement of the slider such that the part to be subjected to X-ray imaging corresponds to a respective position of at least one of the X-ray tube and the X-ray detector.

The recognizing the part to be subjected to X-ray imaging from the generated image of the object may include recognizing a marker which is located at the part to be subjected to X-ray imaging from the generated image of the subject.

The controlling the movement of the slider may include pre-storing information relating to a relative position between the generated image of the subject and at least one of the X-ray tube and the X-ray detector and calculating a control amount for causing the slider to move based on the pre-stored information relating to the relative position.

The calculating the control amount for causing the slider to move may include calculating a control amount for causing the slider to move such that a position of the marker corresponds to at least one of the X-ray tube and the X-ray detector.

The recognizing the part to be X-ray imaging of the object may include pre-storing information relating to a feature of the part to be subjected to X-ray imaging and recognizing the feature from the generated image of the subject.

BRIEF DESCRIPTION OF THE DRAWINGS

These and/or other aspects will become apparent and more readily appreciated from the following description of the exemplary embodiments, taken in conjunction with the accompanying drawings of which.

DETAILED DESCRIPTION

Hereinafter, an X-ray imaging apparatus according to an exemplary embodiment will be described with reference to the accompanying drawings.

Figure 1:
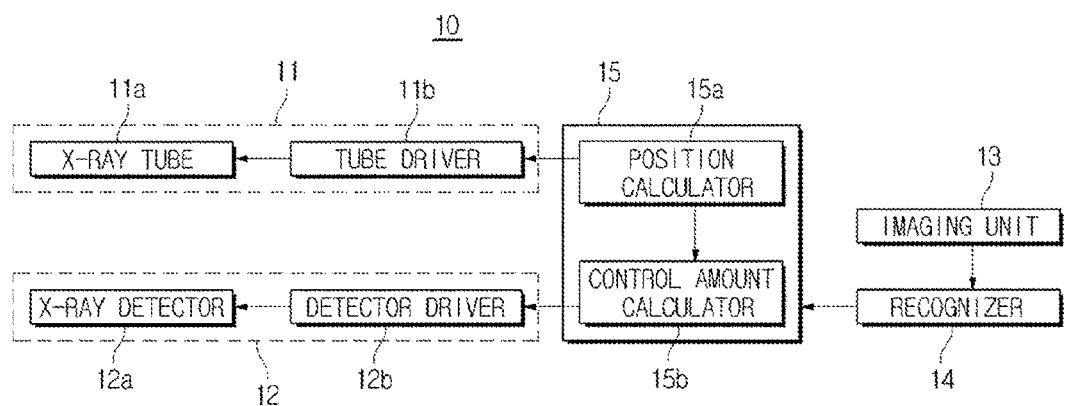
FIG. 1 is a block diagram which illustrates an X-ray imaging apparatus, according to an exemplary embodiment.

FIG. 1 is a block diagram which illustrates an X-ray imaging apparatus, according to an exemplary embodiment.

Referring to FIG. 1, the X-ray imaging apparatus includes an X-ray tube unit 11 which generates and radiates X-rays toward a subject, an X-ray detection unit 12 which detects X-rays which propagate through the subject, an imaging unit 13 which generates an image of the subject, a recognizer 14 which analyzes the image of the subject which is generated by the imaging unit 13 and which recognizes a part to be subjected to X-ray imaging, and a position controller 15 which includes a position calculator 15a and a control amount calculator 15b which match the respective positions of an X-ray tube 11a and an X-ray detector 12a with the position of the part to be subjected to the X-ray imaging.

If the imaging unit 13 generates an image of the subject and transmits the image of the subject to the recognizer 14, the recognizer 14 recognizes the part to be subjected to X-ray imaging from the image of the subject. In recognition of the part to be subjected to X-ray imaging, the part to be subjected to X-ray imaging or a marker located at the part to be subjected to X-ray imaging may be recognized. If the recognizer 14 transmits a result of the recognizing to the position controller 15, the position calculator 15a of the position controller 15 calculates the position of the recognized marker or the part to be subjected to X-ray imaging, and the control amount calculator 15b calculates a control amount to match the respective positions of each of the X-ray tube 11a and an X-ray detector 12a with the position of the part to be subjected to X-ray imaging. The control amount is transmitted to a tube driver 11b and a detector driver 12b, both of which are driven by a driving device, such as, for example, a motor.

Hereinafter, an exemplary embodiment of an X-ray imaging apparatus for recognizing a marker and an exemplary embodiment of an X-ray imaging apparatus for recognizing a part to be subjected to X-ray imaging will be described.

Figure 2:
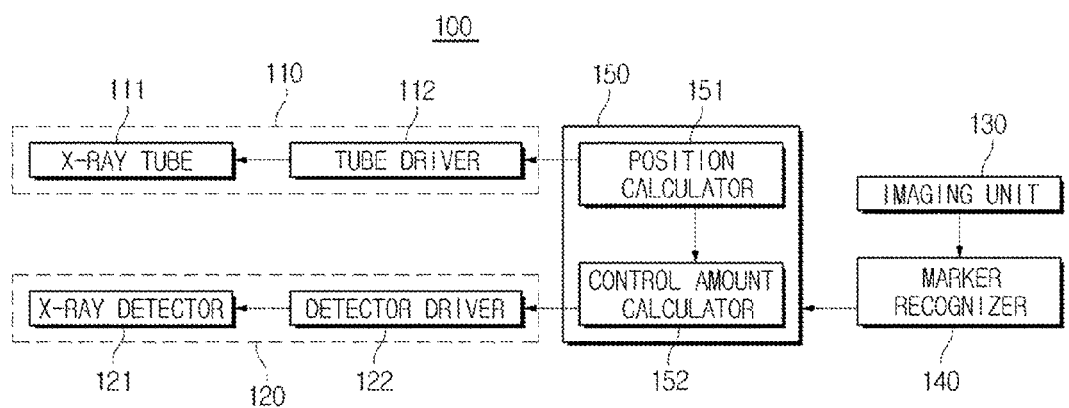
FIG. 2 is a block diagram which illustrates an X-ray imaging apparatus which recognizes a marker, according to an exemplary embodiment.
Figure 3A:
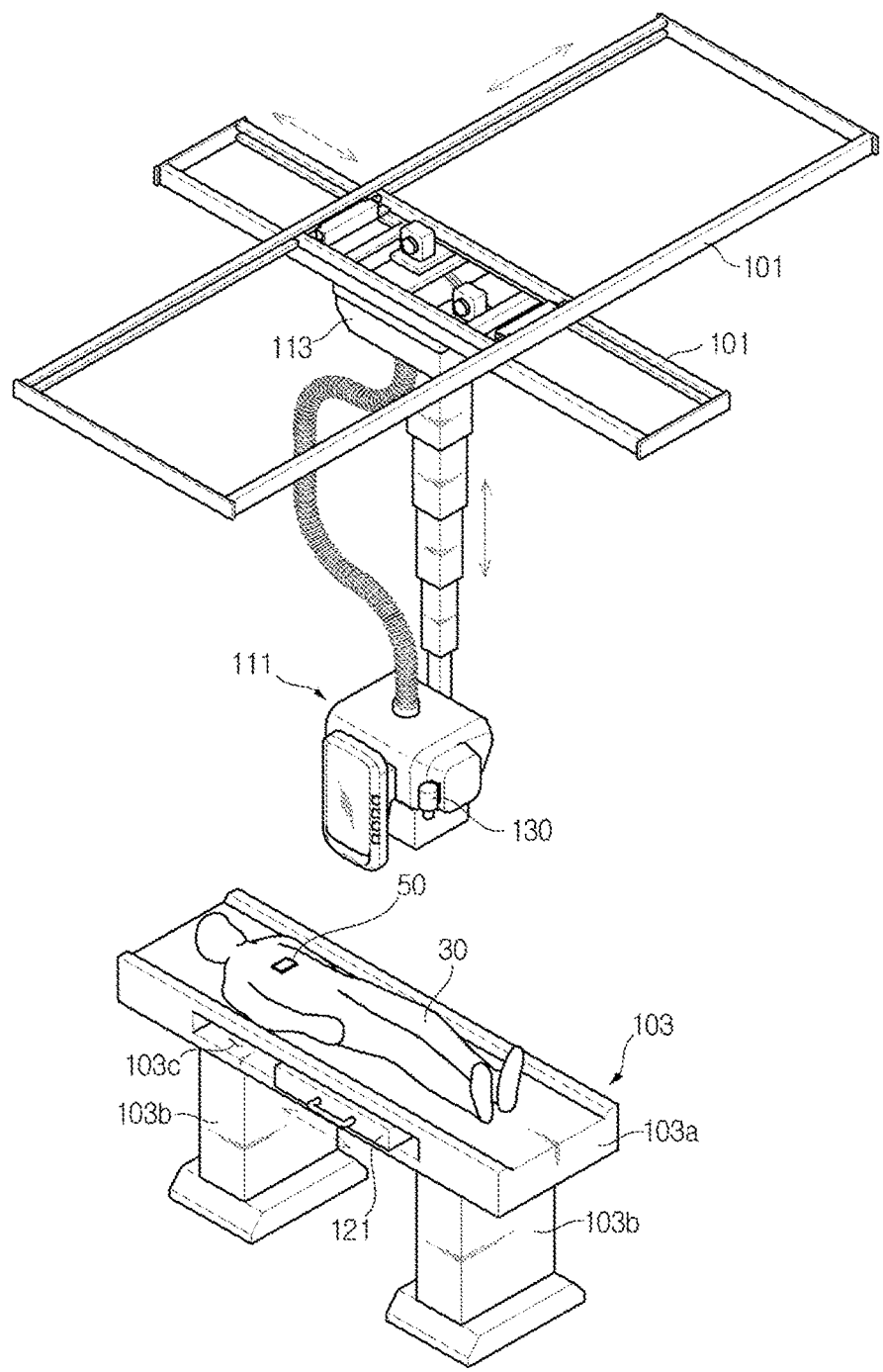
FIGS. 3A and 3B are diagrams which illustrate an appearance of an X-ray imaging apparatus, according to an exemplary embodiment.
Figure 3B:
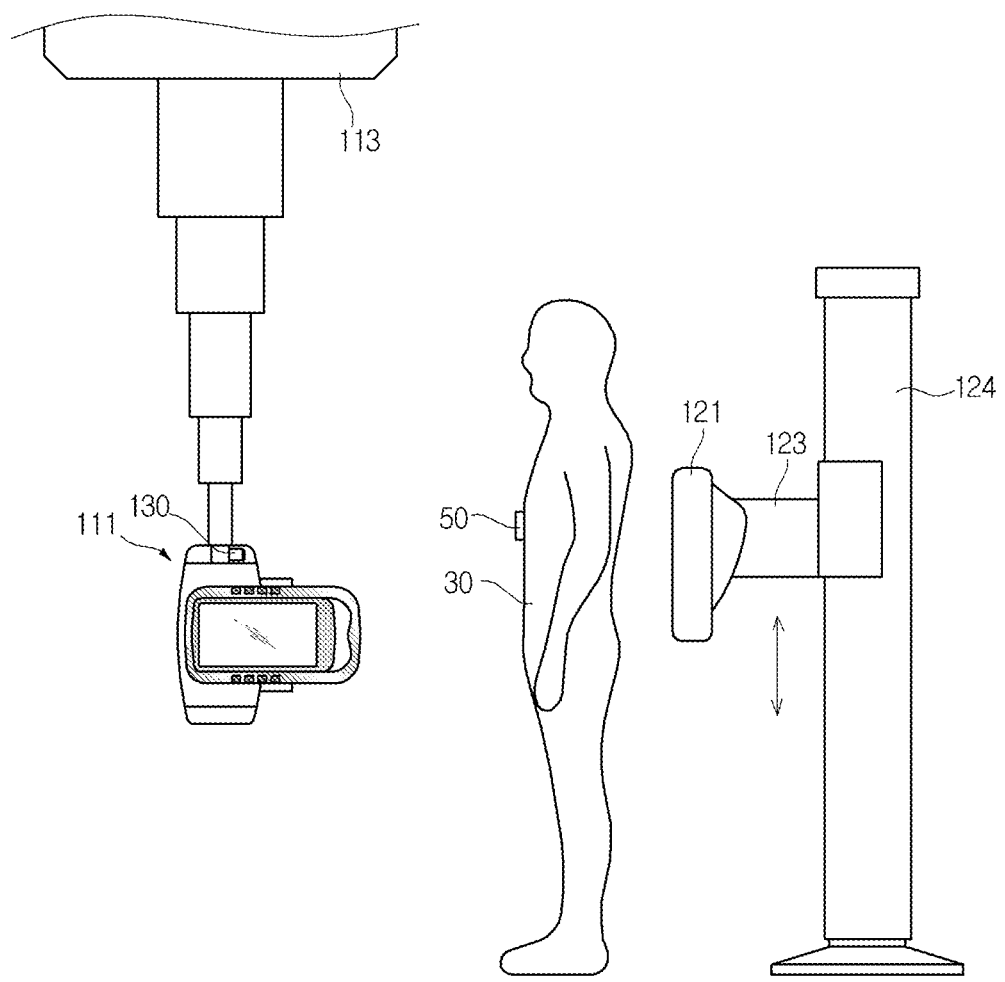

FIG. 2 is a block diagram which illustrates an X-ray imaging apparatus which recognizes a marker, according to an exemplary embodiment, and FIGS. 3A and 3B are diagrams which illustrate an appearance of an X-ray imaging apparatus, according to an exemplary embodiment. Hereinafter, an operation of the X-ray imaging apparatus according to the exemplary embodiment will be described with reference to FIGS. 2, 3A, and 3B.

The X-ray imaging apparatus 100 according to the exemplary embodiment includes an X-ray tube unit 110 which generates and radiates X-rays toward a subject, an X-ray detection unit 120 which detects X-rays which propagate through the subject, an imaging unit 130 which generates an image of the subject, a marker recognizer 140 which analyzes the image of the subject which is generated by the imaging unit 13 and which recognizes a marker, and a position controller 150 which includes a position calculator 151 and a control amount calculator 152 and which moves each of an X-ray tube 111 and an X-ray detector 121 to a respective position which corresponds to the recognized marker.

The X-ray tube unit 110 includes an X-ray tube 111 which generates and radiates X-rays toward the subject and a first tube driver 112 which moves the X-ray tube 111.

Energy of X-rays to be generated by the X-ray tube 111 may be set based on the part of the subject 30 to be subjected to X-ray imaging or based on the purpose of the X-ray imaging. The X-ray tube 111 receives power from a power supply (not shown) and generates X-rays. Energy of X-rays may be controlled by a tube voltage, and the X-ray intensity or dose may be controlled by a tube voltage and an X-ray exposure time.

The X-ray tube 111 may radiate monochromatic X-rays or polychromatic X-rays. If the X-ray tube 111 radiates polychromatic X-rays, the energy band of the radiated X-rays may be defined by an upper limit and a lower limit.

The upper limit of the energy band, that is, a maximum energy of the radiated X-rays is controlled by the level of the tube voltage and the lower limit of the energy band, and a minimum energy of the radiated X-rays may be controlled by a filter provided inside or outside of the X-ray tube 111. If X-rays of a low energy band are filtered by the filter, an average energy of the radiated X-rays may be increased.

As shown in FIGS. 3A and 3B, the X-ray tube 111 is connected to a movement cartridge 113, and the movement cartridge 113 may be moved along a rail 101 which is mounted on the ceiling of an inspecting room in a horizontal direction or a vertical direction. Accordingly, if the first tube driver 112 drives the movement cartridge 113, the X-ray tube 111 connected to the movement cartridge 113 is also moved. In particular, the X-ray tube 111 may be moved by movement of the movement cartridge 113 connected to the X-ray tube 111, and the first tube driver 112 drives the X-ray tube 111 through the movement cartridge 113. The vertical direction corresponds to the longitudinal direction of a patient table 103, and the horizontal direction is perpendicular to the longitudinal direction of the patient table.

The X-ray detection unit 120 includes an X-ray detector 121 which detects X-rays which propagate through the subject and a second detector driver 122 which drives the X-ray detector 121 in the vertical direction.

The X-ray detector 121 detects X-rays which propagate through the subject, converts the detected X-rays into an electrical signal, and acquires X-ray data. In an exemplary embodiment, the X-ray detector 121 may include a light receiving element which generates charges when an X-ray photon is absorbed and a reading circuit which reads and processes an electrical signal from the generated charges. Examples of a material used in the light receiving element may include one of or more a-Si, a-Se, CdZnTe, HgI2, PbI2, and/or any other suitable material.

The operation of the X-ray detector 121 may be divided into a charge integration mode for storing charges for a predetermined time based on a method for acquiring an electrical signal and then acquiring a signal therefrom, and a photon counting mode for performing counting when a signal is generated by a single X-ray photon. Any of the above-described methods may be applied to the X-ray detector 121, according to the exemplary embodiment.

The X-ray imaging apparatus may use a first mode for performing X-ray imaging in a state in which a subject is located on the patient table 103 and a second mode for performing X-ray imaging in a state in which a subject stands between an X-ray tube and an X-ray detector. As shown in FIGS. 3A and 3B, the above-described two modes may be applied to the X-ray imaging apparatus 100 according to the exemplary embodiment.

In the first mode for performing X-ray imaging in a state in which a subject 30 is located on the patient table 103, as shown in FIG. 3A, an upper plate 103a is supported by a support 103b, and a space 103c into which the X-ray detector 121 is inserted and moved in the vertical direction is provided under the upper plate 103a. The X-ray detector 121 is inserted into the space 103c provided under the upper plate 103a to be moved by the second detector driver 122 in the vertical direction.

In the second mode for performing X-ray imaging in a state in which the subject 30 stands between the X-ray tube 111 and the X-ray detector 121, as shown in FIG. 3B, the X-ray detector 121 is connected to a slider 123, and the slider 123 is mounted on a support 124 to be moved by the second detector driver 122 upward or downward.

As described above, the X-ray tube 111 and the X-ray detector 121 may be moved, and the X-ray tube 111 and the X-ray detector 121 should be moved to a position which corresponds to the part to be subjected to X-ray imaging before commencing the X-ray imaging. If a user directly moves the X-ray tube 111 and the X-ray detector 121, user fatigue and the likelihood of having to repeat the X-ray imaging are increased. The X-ray imaging apparatus 100 according to the exemplary embodiment may generate an image of a marker 50 when the user locates the marker 50 on the part of the subject to be subjected to X-ray imaging, and then move each of the X-ray tube 111 and the X-ray detector 121 to a respective position which corresponds to the position of the marker 50. Hereinafter, generating an image of the marker and moving the X-ray tube 111 and the X-ray detector 121 will be described in detail.

Before commencing X-ray imaging, a user, such as, for example, a radiologist or doctor, may locate the marker 50 on the part of the subject to be subjected to X-ray imaging. Any one of the color, material, size, and shape of the marker 50 is not limited, provided that the marker recognizer 140 can recognize the marker from the image which is generated by the imaging unit 130.

For example, the marker 50 may have a polygonal shape, as shown in FIGS. 3A and 3B, or any one of other shapes so long as the marker can be recognized by using a pre-stored recognition algorithm.

The color of the marker 50 is not limited so long as the marker can be recognized by using a color recognition algorithm.

The material of the marker 50 may include, but is not limited to, any one or more of fiber, metal, plastic, rubber, a part of a human body, such as a finger, and/or any other suitable material. If the material of the marker 50 influences the propagation of X-rays, the marker 50 may be removed from the subject 30 after the X-ray tube 111 and the X-ray detector 121 are moved to target positions.

The size of the marker is not limited, and the position of the marker and a control amount may be easily calculated if the size of the marker is not greater than the size of the part to be subjected to X-ray imaging or an X-ray radiation region.

If the subject 30 lies as shown in FIG. 3A, the marker 50 may be placed on the subject 30 and, if the subject 30 stands as shown in FIG. 3B, the user or the subject 30 may hold the marker 50, or the marker 50 may be fixed to the part to be subjected to X-ray imaging by using a fixing member, such as, for example, an adhesive or a string.

If the marker 50 is located on the part to be subjected to X-ray imaging, the imaging unit 130 generates an image of the subject. The imaging unit 130 may be implemented by a camera which is a general imaging apparatus. For example, the imaging unit may include, but is not limited to, at least one of a charge-coupled device (CCD) camera, a complementary metal-oxide-semiconductor (CMOS) camera, and/or any other suitable type of device which can be used to generate an image, in the exemplary embodiment.

As shown in FIGS. 3A and 3B, the imaging unit 130 may be mounted on the X-ray tube 111 and the exemplary embodiment is not limited thereto. The imaging unit 130 may be mounted on the ceiling of an inspecting room in order to generate an image of the subject 30, or may be supported by a support at a position adjacent to the subject 30 in order to generate an image of the subject 30. The position of the imaging unit 130 is not limited, provided that the subject 30 located between the X-ray tube 111 and the X-ray detector 121 can be imaged.

Figure 4:
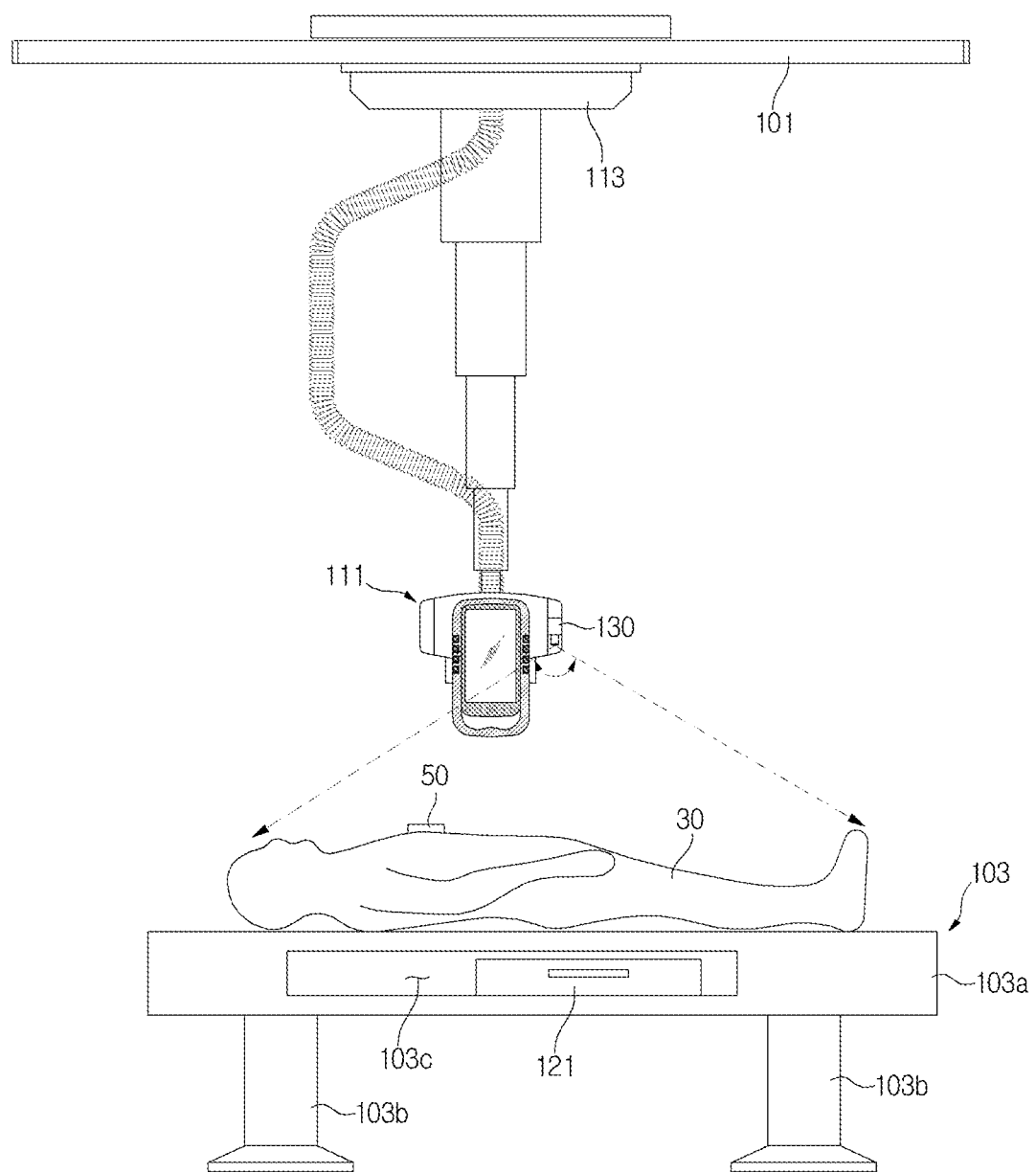
FIG. 4 is a diagram which illustrates an appearance of an X-ray imaging apparatus in a case in which a wide-angle lens is used as an imaging unit.

FIG. 4 is a diagram which illustrates n appearance of an X-ray imaging apparatus in a case in which a wide-angle lens is used as an imaging unit. For convenience of description, in the below-described exemplary embodiment, as shown in FIG. 3A, X-ray imaging is performed in a state in which the subject 30 lies on the patient table 103 and the imaging unit 130 is mounted in the X-ray tube 111.

As an example of the imaging unit 130, a wide-angle camera may be used. The wide-angle camera refers to a camera in which a wide-angle lens having a focal length which is shorter than that of a normal lens is mounted. The shorter the focal length is, the wider is an angle of view. Accordingly, the imaging range of the wide-angle camera is wider that of a corresponding camera having the normal lens. If a wide-angle camera having an angle of view which may cover the length of the patient table 103 is used, as shown in FIG. 4, imaging may be performed over the whole range of the patient table 103 in a single stage.

Because the marker 50 indicates the part of the subject 30 to be subjected to X-ray imaging, only the subject 30 may appear in the image of the subject. However, because patients have different heights, the imaging unit 130 may have an angle of view which covers the length of the upper plate 103a of the patient table 103.

Figure 5A:
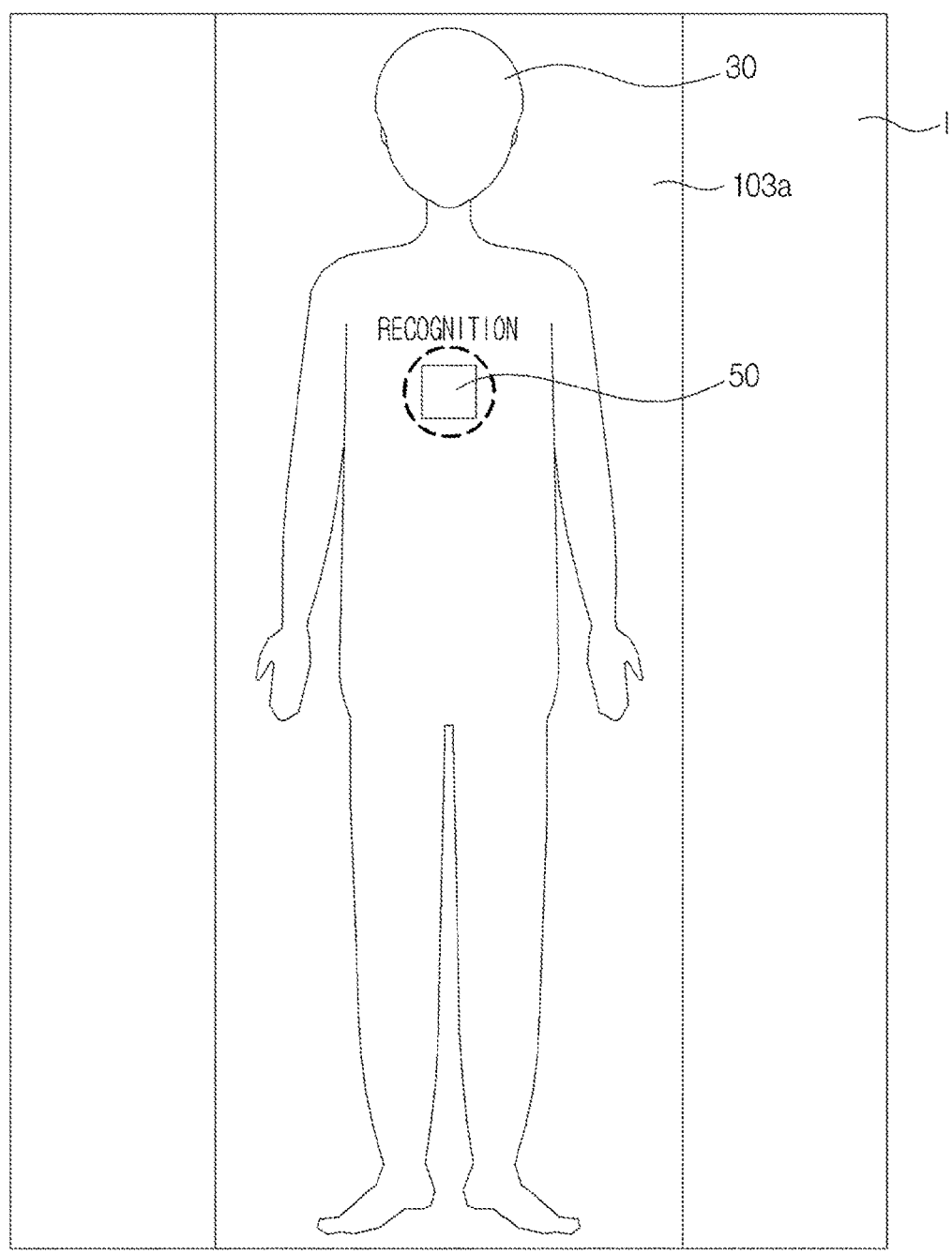
FIGS. 5A and 5B are diagrams which illustrate a recognition of a marker from an image of a subject by a marker recognizer.
Figure 5B:
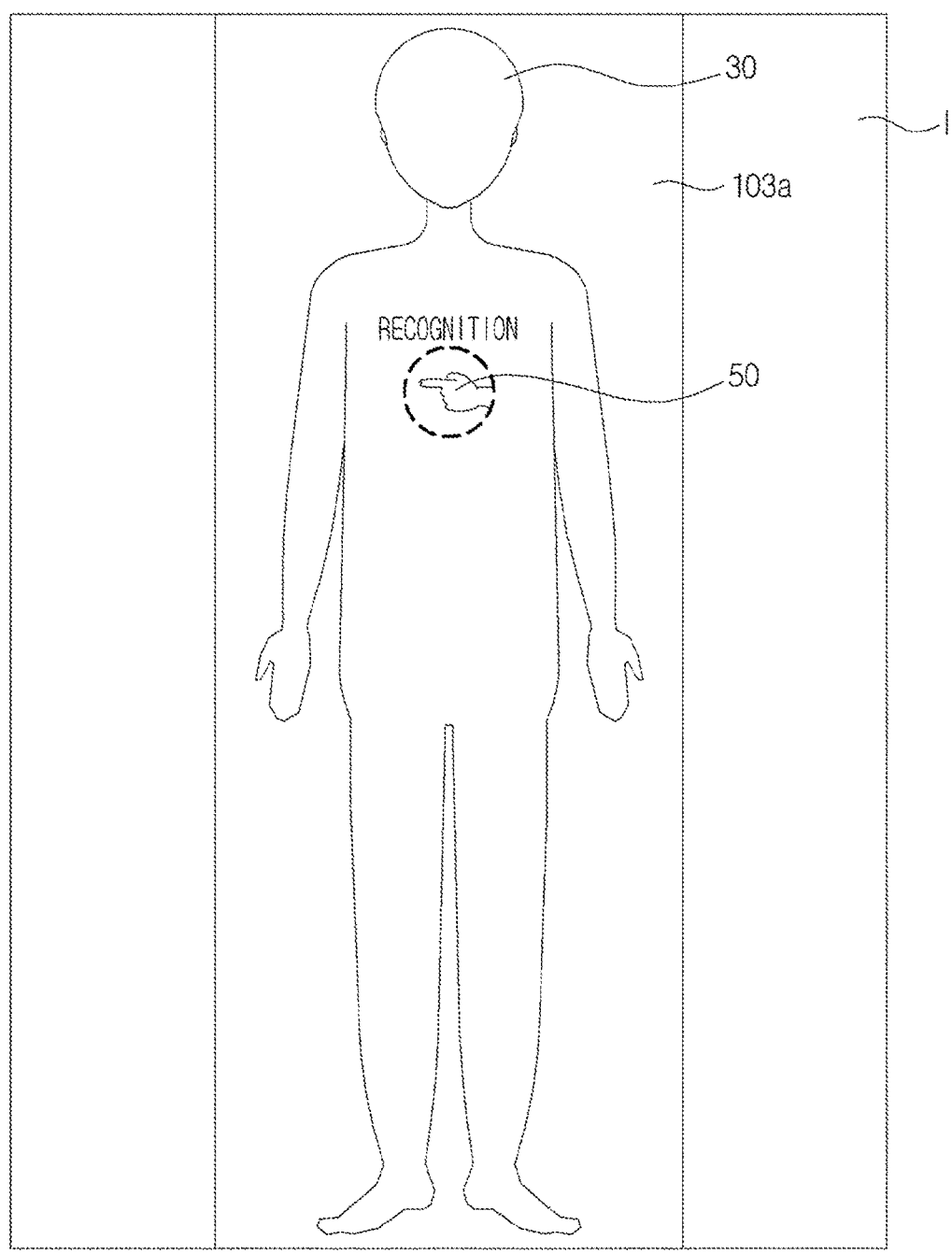

FIGS. 5A and 5B are diagrams which illustrate a recognition of a marker from an image of a subject by a marker recognizer.

The imaging unit 130 transmits the image of the subject to the marker recognizer 140, and the marker recognizer 140 recognizes the marker from the image of the subject. When the marker recognizer 140 recognizes the marker, any of various object recognition algorithms, including a hidden Markov model, may be applicable. Information relating to a feature of the used marker may be pre-stored, and a corresponding feature of the subject which appears in the image of the subject may be extracted and compared with the pre-stored information relating to the feature of the marker, thereby enabling recognition of the marker. The feature used to recognize the marker may include at least one of a shape, a color, a material and a size.

As an example, as shown in FIG. 5A, if information relating to the feature of a rectangle having a predetermined size and shape is pre-stored, the marker recognizer 140 finds a rectangular object having the predetermined size and shape from the image I of the subject. If the rectangular marker 50 having the predetermined size and shape is present in the image I of the subject, the rectangular marker is recognized and the result of the recognition is transmitted to the position controller 150.

As described above, a part of a human body may be used as the marker 50 and, in this case, the user may point to a part to be subjected to X-ray imaging with a finger. In this case, information relating to the finger having a specific shape, as shown in FIG. 5B, may be pre-stored as corresponding to the marker 50. The marker recognizer 140 finds an object having the specific finger shape which corresponds to the pre-stored information in the image I of the subject, recognizes the marker 50 having the specific finger shape if the marker 50 having the specific finger shape is present, and outputs the result of the recognition to the position controller 150.

Figure 6A:
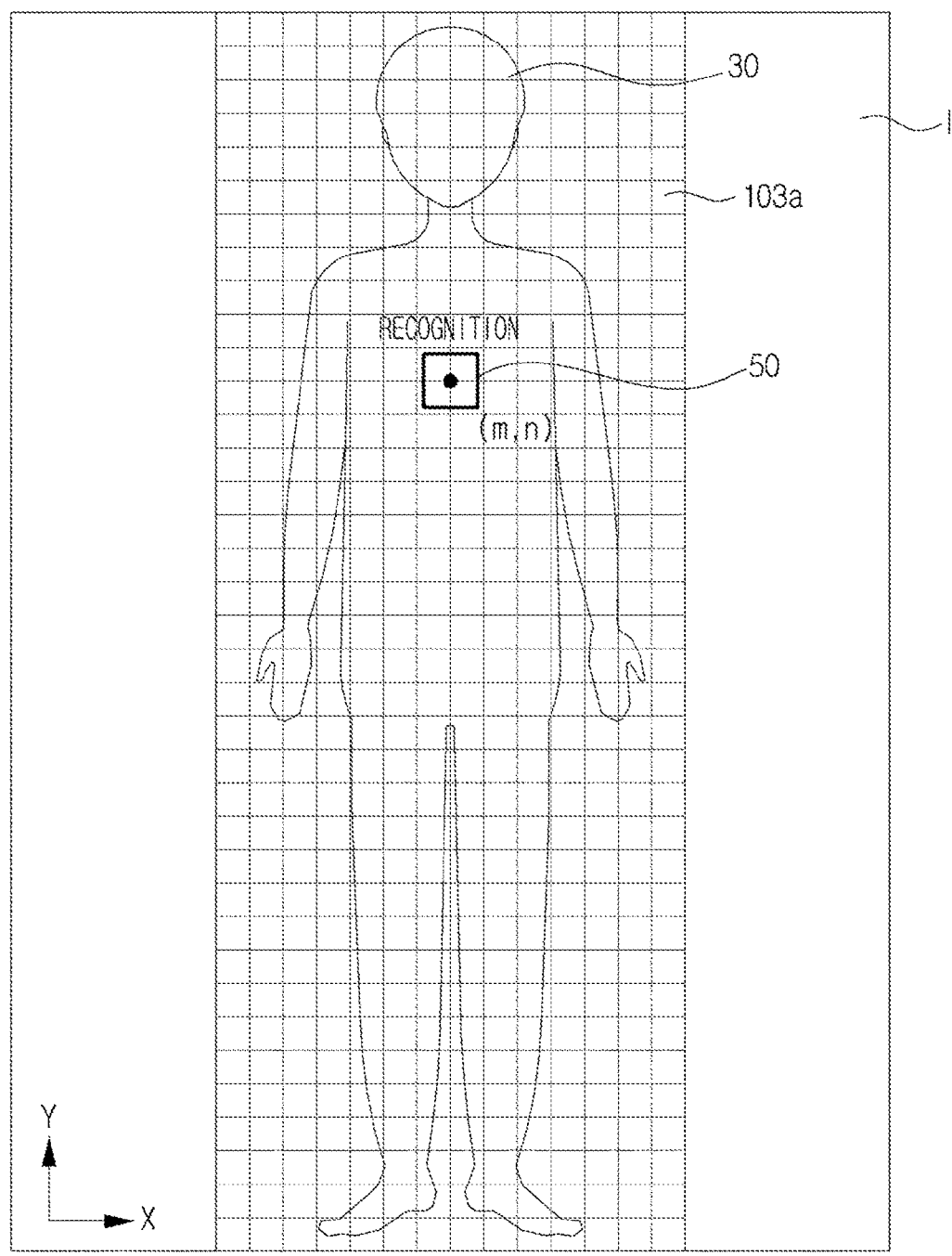
FIG. 6A is a diagram which illustrates a calculation of a position of a marker from an image of a subject by a position controller.
Figure 6B:
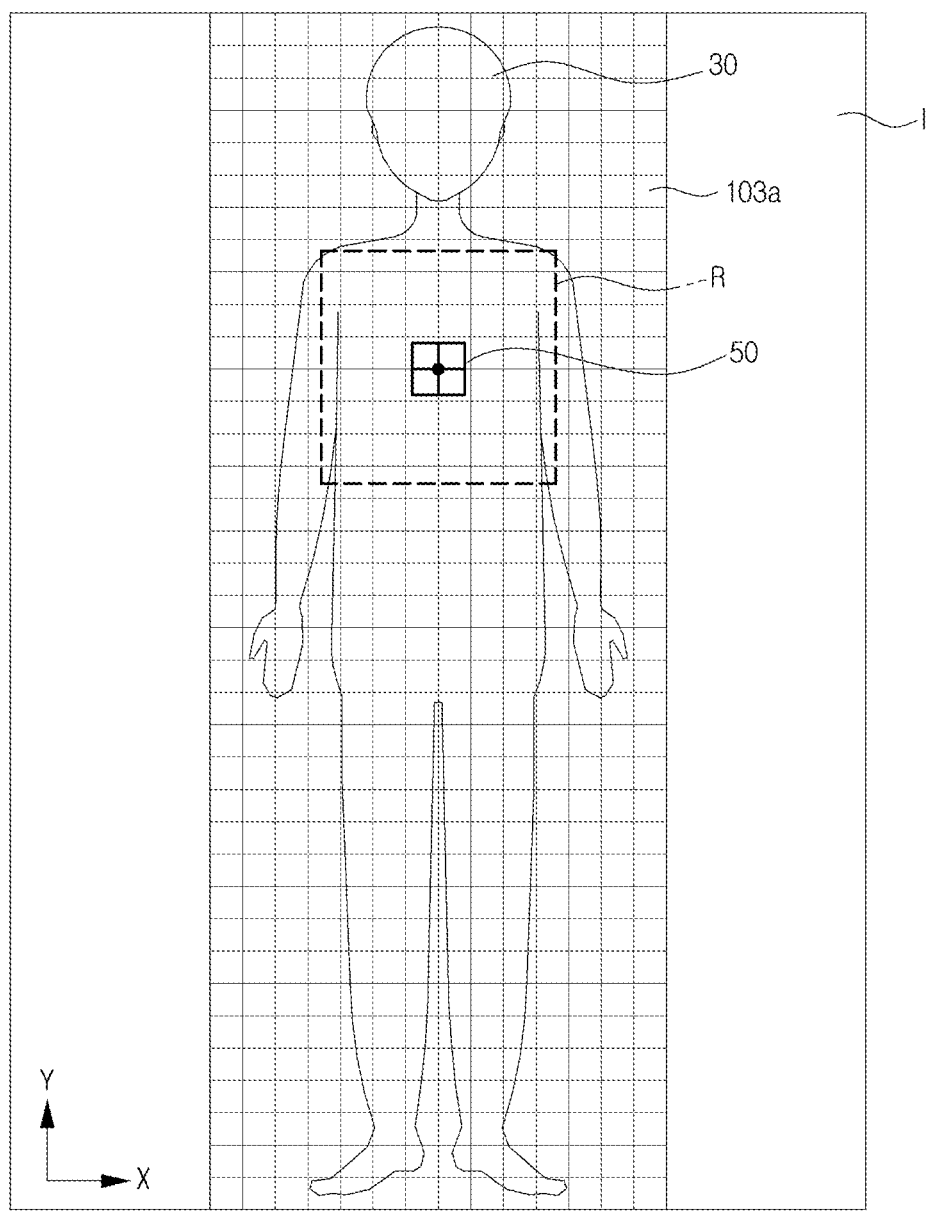
FIG. 6B is a diagram which illustrates an X-ray radiation region which is controlled by a position controller.

FIG. 6A is a diagram which illustrates a calculation of the position of a marker in an image of a subject by the position controller, and FIG. 6B is a diagram which illustrates an X-ray radiation region controlled by the position controller.

As shown in FIG. 2, the position controller 150 includes the position calculator 151 and the control amount calculator 152.

Referring to FIG. 6A, the position calculator 151 calculates the position of the marker 50 which has been recognized by the marker recognizer 140. As an example, the position of the marker 50 may be calculated as coordinates (m, n) of a two-dimensional coordinate system. The image I of the subject may be represented by a two-dimensional coordinate system and, because the marker 50 may be located only in the upper plate 103a, only the internal space of the upper plate 103a may be represented by a two-dimensional coordinate system as shown in FIG. 6A.

The position calculator 151 may complete the calculation of the position of the marker 50 before the X-ray tube 111 and the X-ray detector 121 are moved, or may calculate the position of the marker during a predetermined period or in real time while the X-ray tube 111 and the X-ray detector 121 are being moved to a target position, thereby updating the result.

The latter case is possible if the imaging unit 130 may be mounted in any one of the X-ray tube 111, the movement cartridge 113 or a movable support. While the imaging unit is being moved, the subject is imaged, the marker is recognized and the target position is calculated during a predetermined period or in real time. Because the target position corresponds to the marker 50 and the X-ray tube 111, as the X-ray tube 111 is moved, the imaging unit 130 and the marker 50 may move closer to each other and, as the imaging unit 130 and the marker 50 may move closer to each other, an accuracy of a recognition and a corresponding position calculation with respect to the marker 50 may be improved.

The control amount calculator 152 calculates a control amount for causing the respective positions of each of the X-ray tube 111 and the X-ray detector 121 to correspond with the position of the marker 50. For the calculation of the control amount, the control amount calculator 152 may pre-store information relating to a relative position between the X-ray tube 111 and the subject image I and information relating to a relative position between the X-ray detector 121 and the subject image I. In particular, the actual positions of the X-ray tube 111 and the X-ray detector 121 as expressed by using the coordinate system of the image I of the subject may be pre-stored.

Accordingly, the control amount calculator 152 may acquire the target positions of the X-ray tube 111 and the X-ray detector 121 based on the stored relative position information, and then calculate the required control amount for causing to move the X-ray tube 111 and the X-ray detector 121 to respective target positions. The target positions of the X-ray tube 111 and the X-ray detector 121, more particularly, the positions corresponding to the marker 50, are positions where each of the center of the X-ray radiation region R of the X-ray tube 111 and the center of the detection region of the X-ray detector 121 match the marker 50 or the center of the marker 50 in a two-dimensional space.

The exemplary embodiment is not limited thereto, and the part to be subjected to X-ray imaging as indicated by the marker 50 may be included in the X-ray radiation region in a state in which the center of the marker 50 does not match the radiation region and detection region. More specifically, if the size of the marker 50 exceeds a predetermined size, a portion of the part to be subjected to X-ray imaging may not be imaged when the center of the marker 50 does not match the X-ray radiation region and the X-ray detection region. Accordingly, if the size of the marker 50 is less than the predetermined size, the position of any portion of the region of the marker 50 may be calculated, but, if the size of the marker 50 is greater than the predetermined size, the position of the center of the marker 50 may be calculated.

In order to move the X-ray tube 111 to the target position, the position of the X-ray tube 11 is controlled in each of the vertical direction and the horizontal direction, and each of a vertical-direction control amount and a horizontal-direction control amount for causing the X-ray tube to be moved from a current position to a target position may be calculated. Because the X-ray detector 121 is generally moved only in the vertical direction in the space 130c provided under the upper plate 103a, the control amount calculator 152 may calculate the vertical-direction control amount relating to the X-ray detector 121 in consideration of only the vertical-direction factor of the position of the marker calculated by the position calculator 151. However, this is only an exemplary embodiment, and the horizontal-direction control amount may be calculated if the X-ray detector 121 is movable in the horizontal direction.

If the X-ray imaging apparatus 100 has the structure shown in FIG. 3A, because the X-ray detector 121 is moved upward or downward, the control amount calculator 152 calculates the upward/downward control amount which relates to the X-ray detector 121.

The control amount calculator 152 transmits a driving command which corresponds to the calculated control amount to the tube driver 112 and the detector driver 122. When the tube driver 112 moves the X-ray tube 111 to the target position based on the driving command, as shown in FIG. 6B, the center of the X-ray radiation region R which is displayed by light radiated from the X-ray tube 111 matches the center of the marker 50.

Figure 7:
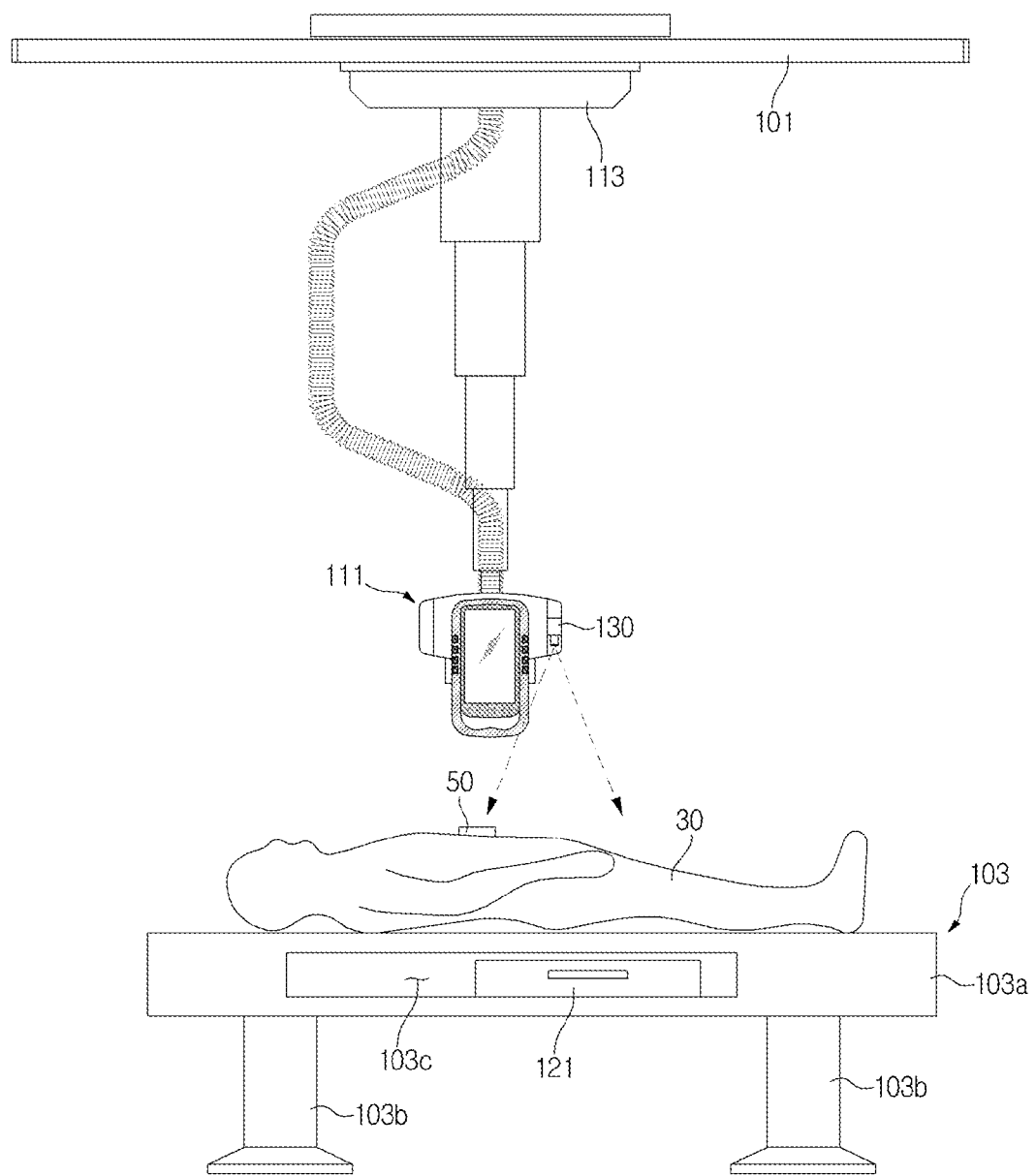
FIG. 7 is a diagram which illustrates an appearance of an X-ray imaging apparatus in a case in which a normal camera is used as an imaging unit instead of a wide-angle camera, according to an exemplary embodiment.
Figure 8:
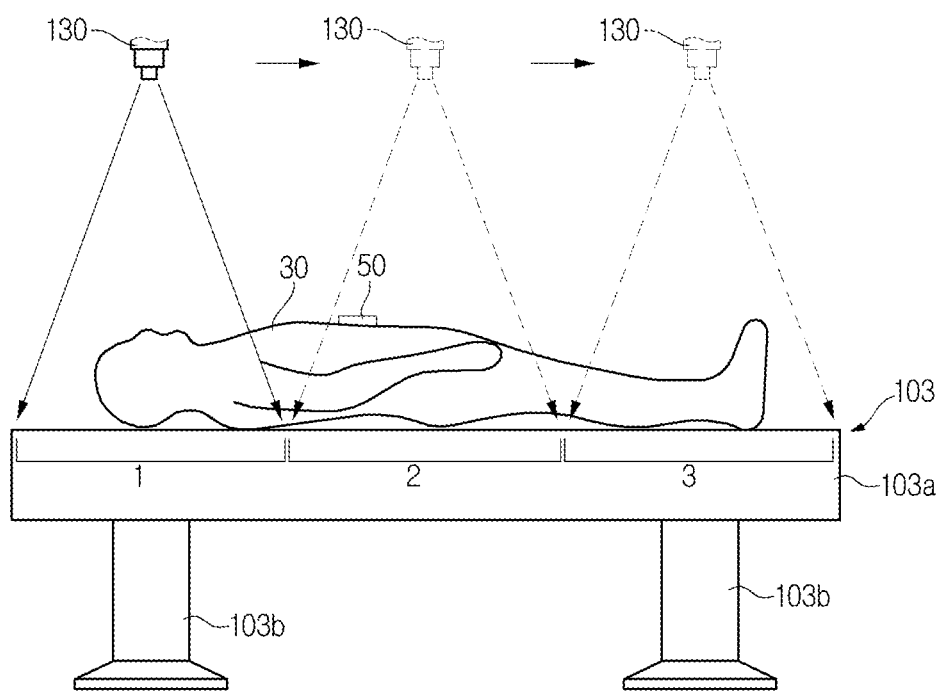
FIG. 8 is a diagram which illustrates a method for generating an image of a subject in a case of using a normal camera.

FIG. 7 is a diagram which illustrates an appearance of an X-ray imaging apparatus in a case in which a normal camera is used as an imaging unit instead of a wide-angle camera according to an exemplary embodiment, and FIG. 8 is a diagram which illustrates a method for generating an image of a subject in a case of using a normal camera.

Although the imaging unit 130 is implemented by a wide-angle camera which is usable for generating an image of the upper plate 103a of the patient table 103 in the above-described exemplary embodiment, the imaging unit 130 may be implemented by a normal camera having a normal lens mounted therein. If the imaging unit 130 is implemented by a normal camera, as shown in FIG. 7, a portion of the upper plate 103a of the patient table 103 or the subject 30 may be imaged in a single stage.

Accordingly, as shown in FIG. 8, while the imaging unit 130 is being moved, segmentation imaging of the upper plate 103a is performed. The number of times of imaging varies based on an angle of view and the length of the upper plate 103a and, for example, if the angle of view of the imaging unit 130 covers one third of the upper plate 103a, as shown in FIG. 8, the imaging unit 130 performs imaging three times while the imaging unit 130 is moved in the longitudinal direction of the upper plate 103a, i.e., the horizontal direction.

If the imaging unit 130 is mounted in the X-ray tube 111, the imaging unit 130 may be moved by moving the X-ray tube 111 and, if the imaging unit 130 is not mounted in the X-ray tube 111, the imaging unit may be moved by using a movable support.

Figure 9A:
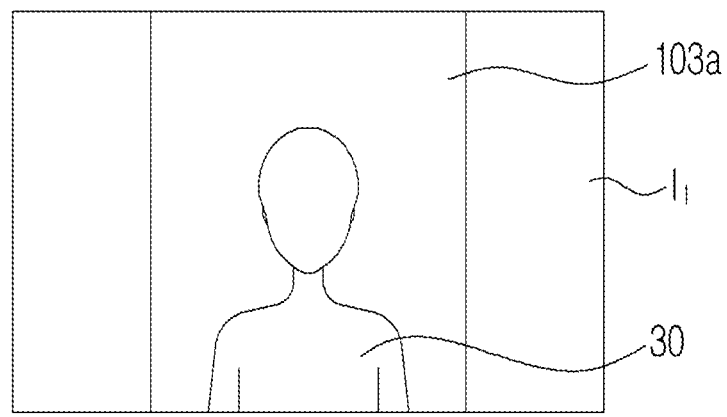
FIGS. 9A, 9B, and 9C are diagrams which illustrate a recognition of a marker from an image of a subject which is generated by using the method illustrated in FIG. 8.
Figure 9B:
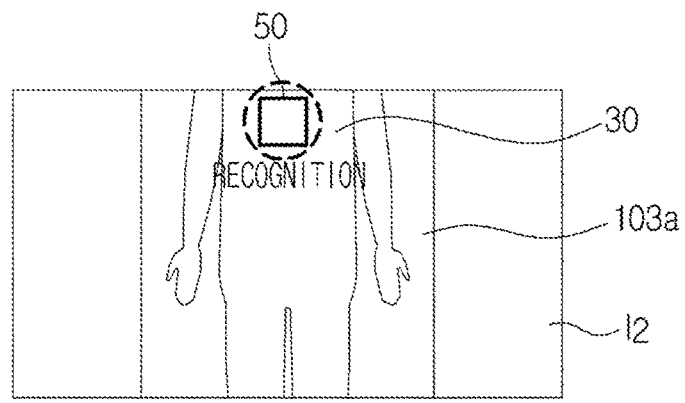
Figure 9C:
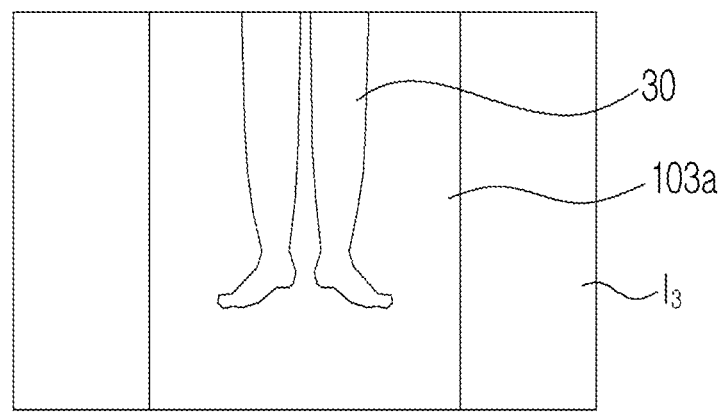

FIGS. 9A, 9B, and 9C are diagrams which illustrate a recognition of a marker 50 from an image of a subject, which image is formed by using the method shown in FIG. 8.

If imaging is performed by using the method shown in FIG. 8, a subject image $I_1$ of a region 1 of FIG. 8, a subject image $I_2$ of a region 2, and a subject image $I_3$ of a region 3 are acquired. If the subject images are transmitted to the marker recognizer 140, the marker recognizer 140 recognizes the marker 50 by using pre-stored information relating to a particular feature of the marker 50 with respect to the subject images $I_1$, $I_2$ and $I_3$ as shown in FIGS. 9A, 9B, and 9C.

Alternatively, the imaging unit 130 transmits the image of the subject which is generated during movement to the marker recognizer 140 in real time in order to recognize the marker in real time. With reference to FIGS. 8, 9A, and 9B, the imaging unit 130 images the region 1 and transmits the image to the marker recognizer 140, the marker recognizer 140 searches for a marker having the feature which corresponds to the pre-stored information in the subject image $I_1$, and the imaging unit 130 is moved to image the region 2 if the marker is not present in the subject image $I_1$. The subject image $I_2$ is transmitted to the marker recognizer 140 and the marker recognizer 140 recognizes the marker 50 having the feature which corresponds to the pre-stored information from the subject image $I_2$. Because the marker 50 is present in the subject image $I_2$, the imaging unit 130 is stopped, and the result of the recognition is transmitted to the position controller 150.

The position calculator 151 calculates the position of the marker 50 in the subject image $I_2$ and the control amount calculator 152 calculates a control amount for causing each of the X-ray tube 111 and the X-ray detector 121 to be moved to the respective positions which correspond to the marker 50. Position calculation and control amount calculation have been described above, and the control amount may be calculated in consideration of the relative position between the space of each subject image subjected to segmentation imaging and the imaging unit 130.

Figure 10:
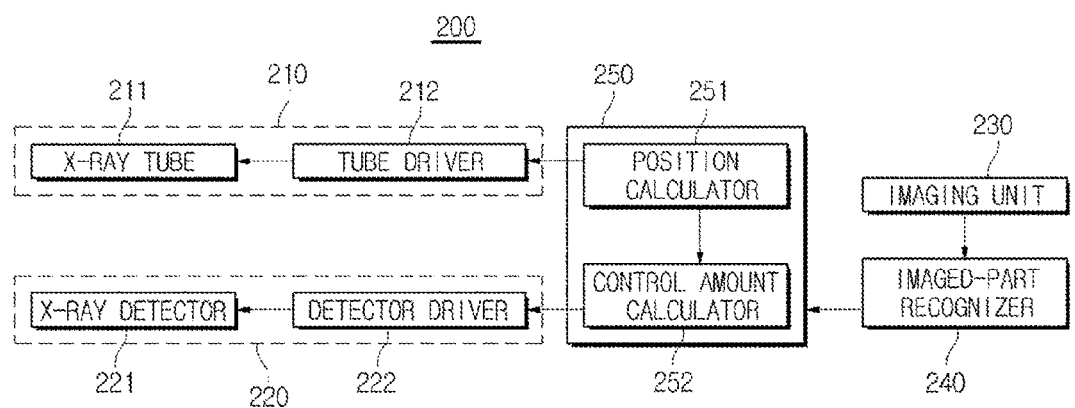
FIG. 10 is a block diagram which illustrates an X-ray imaging apparatus which recognizes a part to be subjected to X-ray imaging, according to another exemplary embodiment.
Figure 11:
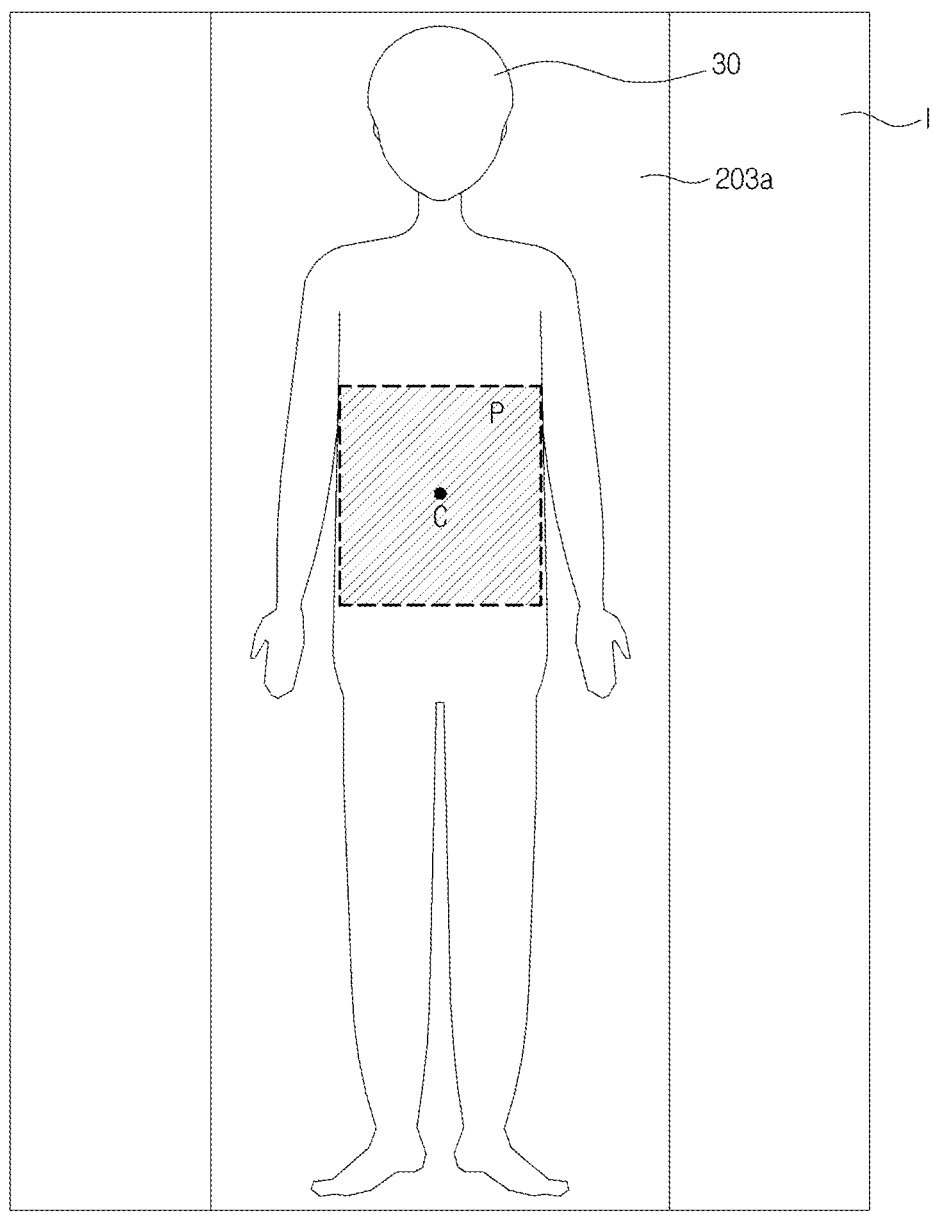
FIG. 11 is a diagram which illustrates a recognition of a part to be subjected to X-ray imaging from an image of a subject.

FIG. 10 is a block diagram which illustrates an X-ray imaging apparatus which recognizes a part to be subjected to X-ray imaging, according to another exemplary embodiment, and FIG. 11 is a diagram which illustrates a recognition of a part to be subjected to X-ray imaging from an image of a subject.

Referring to FIG. 10, the X-ray imaging apparatus 200 according to another exemplary embodiment includes an X-ray tube unit 210 which generates and radiates X-rays toward a subject, an X-ray detection unit 220 which detects X-rays which propagate through the subject, an imaging unit 230 which generates an image of the subject, an imaged-part recognizer which analyzes the image of the subject which is generated by the imaging unit 230 and which recognizes a part to be subjected to X-ray imaging, and a position controller 250 which includes a position calculator 251 and a control amount calculator 252 and which matches the respective positions of each of an X-ray tube 211 and an X-ray detector 221 with the position of the part to be subjected to X-ray imaging.

Although the X-ray imaging apparatus 100 indirectly recognizes the part to be subjected X-ray imaging by using the marker as described above with respect to the exemplary embodiment illustrated in FIG. 2, the X-ray imaging apparatus according to the present exemplary embodiment directly recognizes the part to be subjected to X-ray imaging.

The X-ray tube unit 210, the X-ray detection unit 220 and the imaging unit 230 have been described above with respect to the above-described exemplary embodiment. Hereinafter, an operation of the imaged-part recognizer 240 and the position controller 250 will be described.

Referring also to FIG. 11, if the imaging unit 230 employs a wide-angle camera, generates an image of the subject in a state in which the subject 30 lies on the patient table 203a and transmits the image of the subject to the marker recognizer 240, the marker recognizer 240 finds and recognizes the part P to be subjected to X-ray imaging, as shown in FIG. 11. At this time, the marker recognizer 240 may use at least one of various object recognition algorithms, pre-store information relating to a feature which indicates the part P to be subjected to X-ray imaging, and recognize a region having the feature to which the pre-sored information relates.

The feature which indicates the part P to be subjected to X-ray imaging may include an overall shape of the part to be subjected to X-ray imaging and a physical feature of the part to be subjected to X-ray imaging. For example, if the part to be subjected to X-ray imaging is an arm, a leg or a head, the feature which indicates the part P to be subjected to X-ray imaging may be the shape of the arm, the leg or the head, or the position of the arm, the leg or the head with respect to the subject 30. The imaged-part recognizer 240 recognizes a region having a feature to which the pre-stored information relates from the subject image, and the position calculator 251 calculates the position of the center of the recognized region.

The control amount calculator 252 calculates a control amount for causing each of the X-ray tube 211 and the X-ray detector 221 to be moved to a respective position which corresponds to the part P to be subjected to X-ray imaging. For calculation of the control amount, information relating to the relative position between the X-ray tube 211 and the subject image I and information relating to the relative position of the X-ray detector 221 and the subject image I may be pre-stored. In particular, the actual positions of the X-ray tube and the X-ray detector as expressed with respect to the coordinate system of the subject image I may be pre-stored.

The control amount calculator 252 may acquire the respective target positions of each of the X-ray tube 211 and the X-ray detector 221 based on the stored relative position information, and then calculate the control amount for causing each of the X-ray tube 211 and the X-ray detector 221 to be moved to the respective target positions. The target positions of the X-ray tube 211 and the X-ray detector 221, more particularly, the positions which respectively correspond to the part to be subjected to X-ray imaging, may be the positions where the center of the X-ray radiation region of the X-ray tube 211 and the center of the detection region of the X-ray detector 221 match the part to be subjected to X-ray imaging or the center of the part to be subjected to X-ray imaging in a two-dimensional space.

As an example, the control amount for causing each of the center of the X-ray radiation region of the X-ray tube 211 and the center of the detection region of the X-ray detector 221 to match with the center C of the part P to be subjected to X-ray imaging may be calculated.

However, the position calculator 251 may not calculate the position of the center of the part P to be subjected to X-ray imaging. More specifically, if the size of the part P to be subjected to X-ray imaging is equal to or greater than a predetermined size, a portion of the part to be subjected to X-ray imaging may not be imaged when the centers of the X-ray radiation region and the X-ray detection region do not match the center of the center of the part P to be subjected to X-ray imaging. Accordingly, although the position of any portion of the regions of the part P to be subjected to X-ray imaging may be calculated if the size of the part P to be subjected to X-ray imaging is less than the predetermined size, the position of the center of the part P to be subjected to X-ray imaging is calculated if the size of the part P to be subjected to X-ray imaging is equal to or greater than the predetermined size.

As another example, if the part P to be subjected to X-ray imaging is an abdomen, the imaged-part recognizer 240 may recognize a navel of the subject image I as a feature, the position calculator 251 may calculate the position of the navel, and the control amount calculator 252 may calculate a control amount for causing each of the X-ray tube 211 and the X-ray detector 221 to be moved to a respective position which corresponds to the navel and then transmit the calculated control amount to the tube driver 212 and the detector driver 222.

Although the X-ray tube 11a and the X-ray detector 12a are fixed during X-ray imaging in the X-ray imaging apparatus 10 according to the above-described embodiment, the exemplary embodiment is not limited thereto. An X-ray imaging apparatus 20 according to another exemplary embodiment may be implemented by a computed tomography (CT) device in which an X-ray tube and an X-ray detector are mounted in a gantry and rotated.

Figure 12:
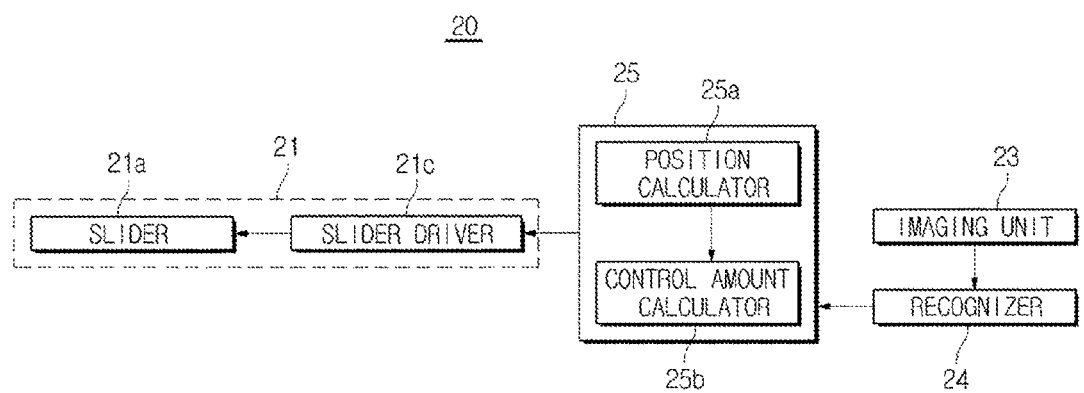
FIG. 12 is a block diagram which illustrates an X-ray imaging apparatus, according to another exemplary embodiment.

FIG. 12 is a block diagram which illustrates an X-ray imaging apparatus according to another exemplary embodiment.

Referring to FIG. 12, the X-ray imaging apparatus 20 according to another exemplary embodiment includes an imaging unit 23 which generates an image of a subject, a marker recognizer 24 which recognizes a marker in the image of the subject, a position controller 25 which determines a part to be subjected to X-ray imaging and controls the position of a slider 21a such that the marker is located between an X-ray tube and an X-ray detector, and a patient table 21 which is controlled by the position controller 25.

If the imaging unit 23 generates an image of the subject and transmits the image of the subject to the recognizer 24, the recognizer 24 recognizes the part to be subjected to X-ray imaging from the image of the subject. In recognition of the part to be subjected to X-ray imaging, the part to be subjected to X-ray imaging or a marker located at the part to be subjected to X-ray imaging may be recognized. If the recognizer 24 transmits the result of the recognition to the position controller 25, the position calculator 25a of the position controller 25 calculates the position of the recognized marker or the part to be subjected to X-ray imaging, and the control amount calculator 25b calculates a control amount for causing the marker or the part to be subjected to X-ray imaging to be positioned between the X-ray tube and the X-ray detector.

The calculated control amount is transmitted to a slider driver 21c, which is implemented by a driving device, such as, for example, a motor.

Hereinafter, an exemplary embodiment of an X-ray imaging apparatus for recognizing a marker and an exemplary embodiment of an X-ray imaging apparatus for recognizing a part to be subjected to X-ray imaging will be described.

Figure 13:
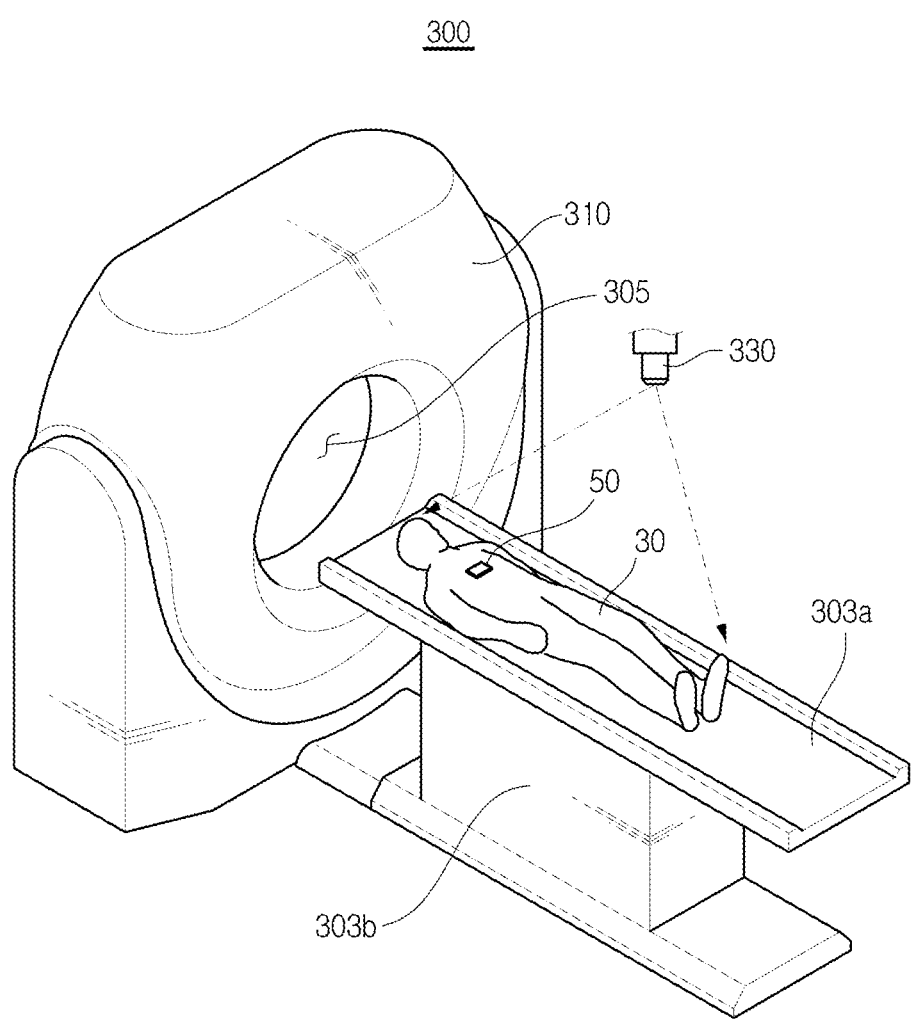
FIG. 13 is a diagram which illustrates an appearance of an X-ray imaging apparatus in a case of using a marker, according to another exemplary embodiment.
Figure 14:
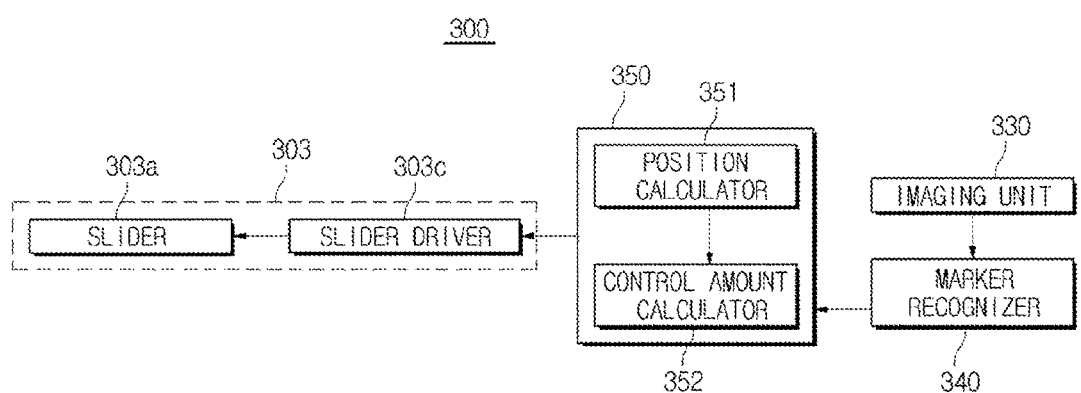
FIG. 14 is a block diagram which illustrates an X-ray imaging apparatus in a case of using a marker, according to another exemplary embodiment.

FIG. 13 is a diagram which illustrates an appearance an X-ray imaging apparatus according to another exemplary embodiment in a case of using a marker, and FIG. 14 is a block diagram which illustrates an X-ray imaging apparatus according to another exemplary embodiment in a case of using a marker.

Referring to FIG. 13, an X-ray tube and an X-ray detector of the X-ray imaging apparatus 300 are mounted in a gantry of a housing 310 and are rotated. The patient table 303 includes a slider 303a supported by a support 303b, and the slider 303a is a bed on which a subject 30 lies and is movable into a bore 305. The X-ray imaging apparatus 300 moves the slider 303a into the bore 305 when the subject 30 lies on the slider 303a, and locates the part to be subjected to X-ray imaging between the X-ray tube and the X-ray detector.

Although a user may directly control the position of the slider 303a, the X-ray imaging apparatus 300 according to another exemplary embodiment automatically moves the slider 303a to a target position.

Referring to FIG. 14, the X-ray imaging apparatus 300 includes an imaging unit 330 which generates an image of a subject, a marker recognizer 340 which recognizes a marker from the image of the subject, a position controller 350 which calculates the position of the marker and controls the position of the slider 303a such that the position of the marker on the slider 303a is located between an X-ray tube and an X-ray detector, and a patient table 303.

Although the imaging unit 330 may be implemented similarly as described above with respect to the imaging units 130 and 230 of the X-ray imaging apparatus 100 and 200 according to the above-described exemplary embodiments, the imaging unit 330 may not be mounted in the X-ray tube but may be mounted on one of the ceiling of an inspecting room and a predetermined support connected to one side of the patient table 303 or the housing 310. The position of the imaging unit 330 is purely exemplary and is not limited, provided that the imaging unit may image the slider 303a or the subject 30 on the slider before the slider 303a is inserted into the bore 305.

The image of the subject which is generated by the imaging unit 330 is transmitted to the marker recognizer 340, and the marker recognizer 340 recognizes the marker 50 which has a particular feature which corresponds to pre-stored information from the image of the subject. Marker type and marker recognition have been described above.

The position controller 350 includes a position calculator 351 and a control amount calculator 352. The position calculator 351 calculates the position of the recognized marker 50, and the control amount calculator 352 calculates a control amount which causes the slider 303a to be moved such that the position of the marker 50 on the slider 303a is located between the X-ray tube and the X-ray detector.

More specifically, the position calculator 351 calculates the position of the marker 50 on the slider 303a. As described above with reference to FIG. 6A, if the position of the marker 50 appearing in the subject image I on the slider 303a is calculated by using two-dimensional coordinates, a determination as to which point of the slider 303a is located between the X-ray tube and the X-ray detector may be made by the position of the marker. For example, if the position of the marker 50 is expressed as (m, n), the position (m, n) of the slider 303a is located between the X-ray tube and the X-ray detector for X-ray imaging.

The control amount calculator 352 calculates a control amount for causing the slider 303a of the patient table to be moved such that the position of the marker 50 matches the position of the X-ray tube 311 or the X-ray detector 321. For calculation of the control amount, information relating to the relative position between the slider 303a and the X-ray tube 311 or the X-ray detector 321 may be pre-stored. The control amount for causing the position of the marker 50 on the slider 303a to be matched with one of the center of the radiation region of the X-ray tube and the center of the detection region of the X-ray detector is calculated based on the stored relative position information. The calculated control amount is transmitted to the slider driver 303c, and the slider driver 303c drives the slider 303a based on the transmitted control amount.

Matching the position of the marker 50 on the slider 303a with the center of the radiation region of the X-ray tube or the center of the detection region of the X-ray detector is equivalent to matching the position of the marker 50 on the slider 303a with the center of the radiation region of the X-ray tube or the center of the detection region of the X-ray detector in a two-dimensional space.

Unlike the X-ray imaging apparatus 100 and 200 according to the above-described exemplary embodiments, because the X-ray imaging apparatus 300 according to the present exemplary embodiment is mounted in the gantry in a state in which the X-ray tube faces the X-ray detector, the position of the slider 303a may match the position of one of the X-ray tube and the X-ray detector.

Figure 15:
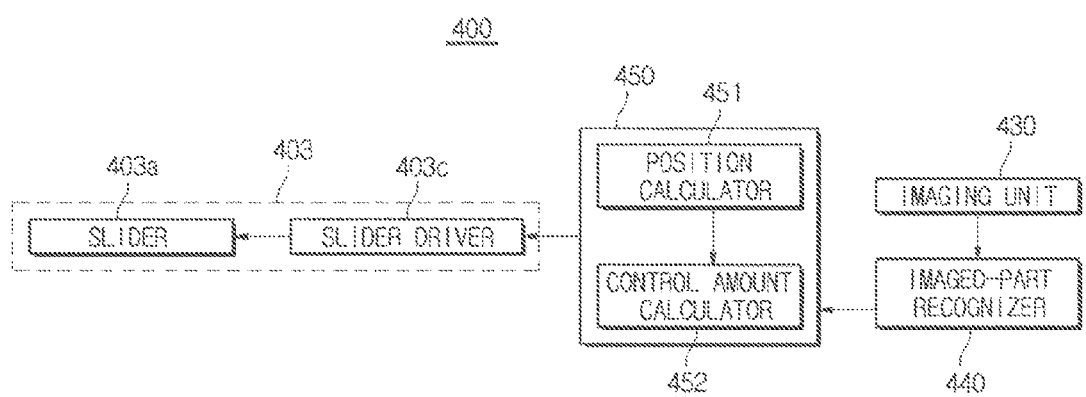
FIG. 15 is a block diagram which illustrates an X-ray imaging apparatus which recognizes a part to be subjected to X-ray imaging, according to another exemplary embodiment.

FIG. 15 is a block diagram which illustrates an X-ray imaging apparatus which recognizes a part to be subjected to X-ray imaging, according to another exemplary embodiment. The appearance of the X-ray imaging apparatus 400 according to the present exemplary embodiment, the configuration and operation of the imaging unit 430 and the configuration and operation of the patient table 403 are equivalent to those of the above-described X-ray imaging apparatus 300.

An imaged-part recognizer 440 uses pre-stored information in order to recognize a part to be subjected to X-ray imaging from the image of the subject which is generated by the imaging unit 430. A description thereof is equivalent to the description of the exemplary embodiment illustrated in FIG. 14.

The position calculator 451 calculates the position of the recognized part to be subjected to X-ray imaging on the slider 303a. The position of the part to be subjected to X-ray imaging may be calculated as two-dimensional coordinates. The position of a portion other than the center of the part to be subjected to X-ray imaging may be calculated if the size of the part to be subjected to X-ray imaging is less than a predetermined size, and the position of the center of the part to be subjected to X-ray imaging is calculated if the size of the part to be subjected to X-ray imaging is equal to or greater than the predetermined size.

The control amount calculator 452 may pre-store information relating to the relative position between the slider 403a and the X-ray tube or the X-ray detector. A control amount for causing the position of the part to be subjected to X-ray imaging on the slider 403a to be matched with the center of the radiation region of the X-ray tube or the center of the detection region of the X-ray detector is calculated based on the stored relative position information. The calculated control amount is transmitted to the slider driver 403c, and the slider driver 403c drives the slider 403a based on the transmitted control amount.

Hereinafter, a method for controlling an X-ray imaging apparatus according to an exemplary embodiment will be described.

Figure 16:
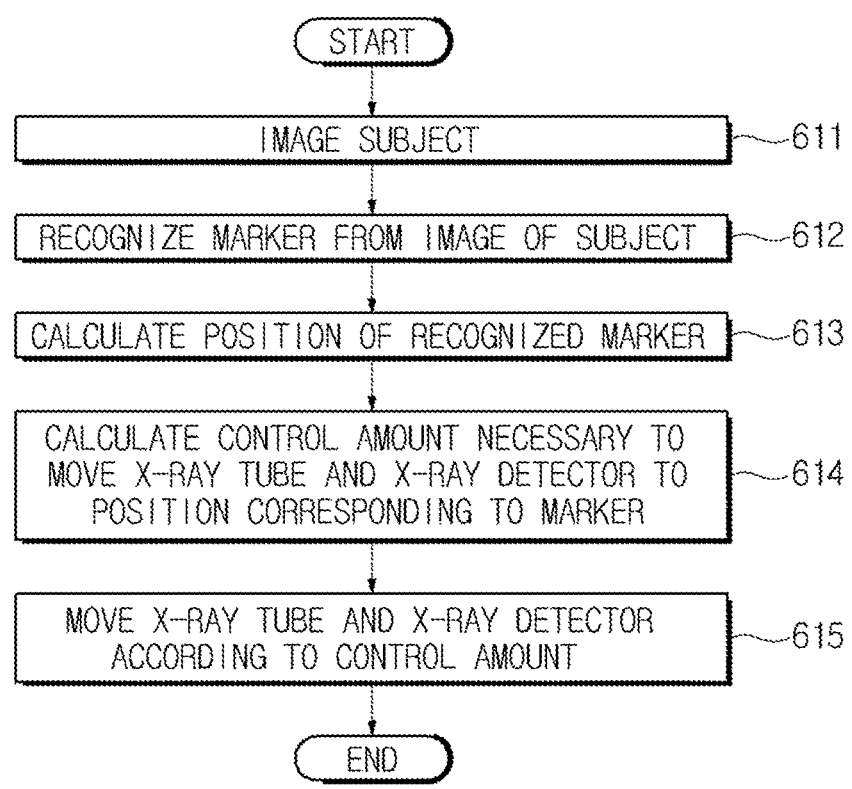
FIG. 16 is a flowchart which illustrates a method for controlling an X-ray imaging apparatus which corresponds to the exemplary embodiment illustrated in FIG. 2.

FIG. 16 is a flowchart which illustrates a method for controlling an X-ray imaging apparatus which corresponds to the exemplary embodiment illustrated in FIG. 2.

Referring to FIG. 16, in operation 611, the subject is imaged by using a camera before commencement of X-ray imaging. The subject is imaged in a state in which preparation for X-ray imaging is completed; in particular, in a state in which the subject is located between the X-ray tube and the X-ray detector, the user locates a marker on the part of the subject to be subjected to X-ray imaging. If the camera is a wide-angle camera which covers an entirety of the subject or the patient table, the subject may be imaged in a single stage and, if the camera is a normal camera which has a normal lens mounted therein, imaging of the subject may be performed in multiple stages.

In operation 612, the marker is recognized from the image of the subject. The marker may be recognized by using at least one of various object recognition algorithms. Information relating to a particular feature of the marker may be pre-stored, and the marker having the particular feature may be recognized from the image of the subject.

In operation 613, the position of the recognized marker is calculated. In one exemplary embodiment, the position of the marker may be calculated as coordinates (m, n) in a two-dimensional coordinate system. Calculation of the position of the marker may be completed before the X-ray tube and the X-ray detector are moved, or the position of the marker may be calculated during a predetermined period or in real time while the X-ray tube and the X-ray detector are being moved to target positions, thereby updating the result.

In operation 614, a control amount for causing each of the X-ray tube and the X-ray detector to be moved to respective positions which correspond to the marker is calculated. For this calculation, information relating to the relative position between the X-ray tube and the subject image and information relating to the relative position between the X-ray detector and the subject image may be pre-stored. In particular, the actual positions of the X-ray tube and the X-ray detector as expressed with respect to the coordinate system of the subject image may be pre-stored. The target positions of the X-ray tube and the X-ray detector may be acquired based on the stored relative position information, and the control amount for causing the X-ray tube and the X-ray detector to be moved to the respective target positions is calculated. The target positions of the X-ray tube and the X-ray detector, more particularly, the positions corresponding to the marker, may be positions where the center of the X-ray radiation region of the X-ray tube and the center of the detection region of the X-ray detector match the marker or the center of the marker in a two-dimensional space.

In operation 615, the X-ray tube and the X-ray detector are moved based on the calculated control amount, and X-ray imaging is performed.

Figure 17:
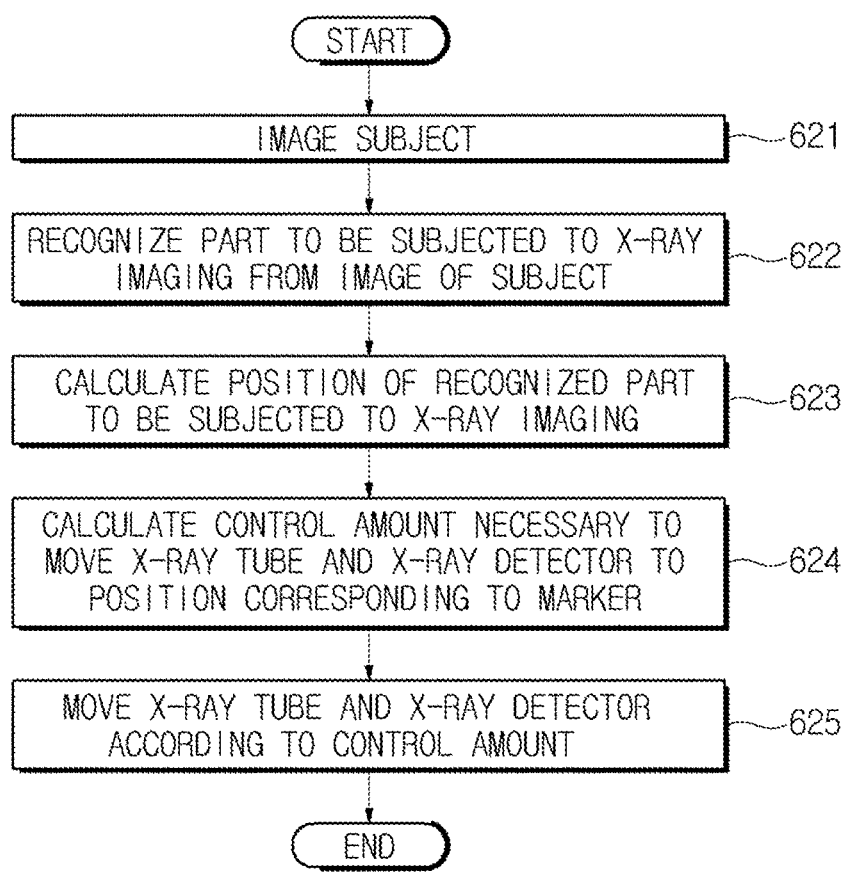
FIG. 17 is a flowchart which illustrates a method for controlling an X-ray imaging apparatus which corresponds to the exemplary embodiment illustrated in FIG. 10.

FIG. 17 is a flowchart which illustrates a method for controlling an X-ray imaging apparatus which corresponds to the exemplary embodiment illustrated in FIG. 10.

Referring to FIG. 17, in operation 621, a subject is imaged by using a camera before X-ray imaging. The subject is imaged in a state in which preparation for X-ray imaging is completed; in particular, in a state in which the subject is located between the X-ray tube and the X-ray detector. The subject may be imaged in a single stage if the camera is a wide-angle camera which is capable of covering an entirety of the subject or the patient table, and may be imaged in multiple stages if the camera is a normal camera which has a normal lens mounted therein.

In operation 622, a part to be subjected to X-ray imaging is recognized from the image of the subject. The part to be subjected to X-ray imaging may be recognized by using at least one of various object recognition algorithms, and information relating to at least one of particular features of the part to be subjected to X-ray imaging may be pre-stored, and the part to be subjected to X-ray imaging which has the particular features may be recognized from the image of the subject.

In operation 623, the position of the recognized part to be subjected to X-ray imaging is calculated. In an exemplary embodiment, the position of the part to be subjected to X-ray imaging may be calculated as coordinates (m, n) of a two-dimensional coordinate system. The position of the part to be subjected to X-ray imaging may be the position of the center of the part to be subjected to X-ray imaging. However, the position of the center of the part to be subjected to X-ray imaging is not necessarily calculated, and the position of an arbitrary portion of the part to be subjected to X-ray imaging may be calculated, based on the size of the part to be subjected to X-ray imaging.

In operation 624, a control amount for causing each of the X-ray tube and the X-ray detector to be moved to the respective positions which correspond to the part to be subjected to X-ray imaging is calculated. Information relating to the relative position between the X-ray tube and the subject image and information relating to the relative position between the X-ray detector and the subject image may be pre-stored. In particular, the actual positions of the X-ray tube and the X-ray detector as expressed with respect to the coordinate system of the subject image may be pre-stored. The target positions of the X-ray tube and the X-ray detector may be acquired based on the stored relative position information, and a control amount for causing the X-ray tube and the X-ray detector to be moved to the respective target positions is calculated. The target positions of the X-ray tube and the X-ray detector, more particularly, the positions corresponding to the part to be subjected to X-ray imaging, may be positions where each of the center of the X-ray radiation region of the X-ray tube and the center of the detection region of the X-ray detector respectively matches the part to be subjected to X-ray imaging or the center thereof in a two-dimensional space.

In operation 625, the X-ray tube and the X-ray detector are moved based on the calculated control amount, and X-ray imaging is performed.

Figure 18:
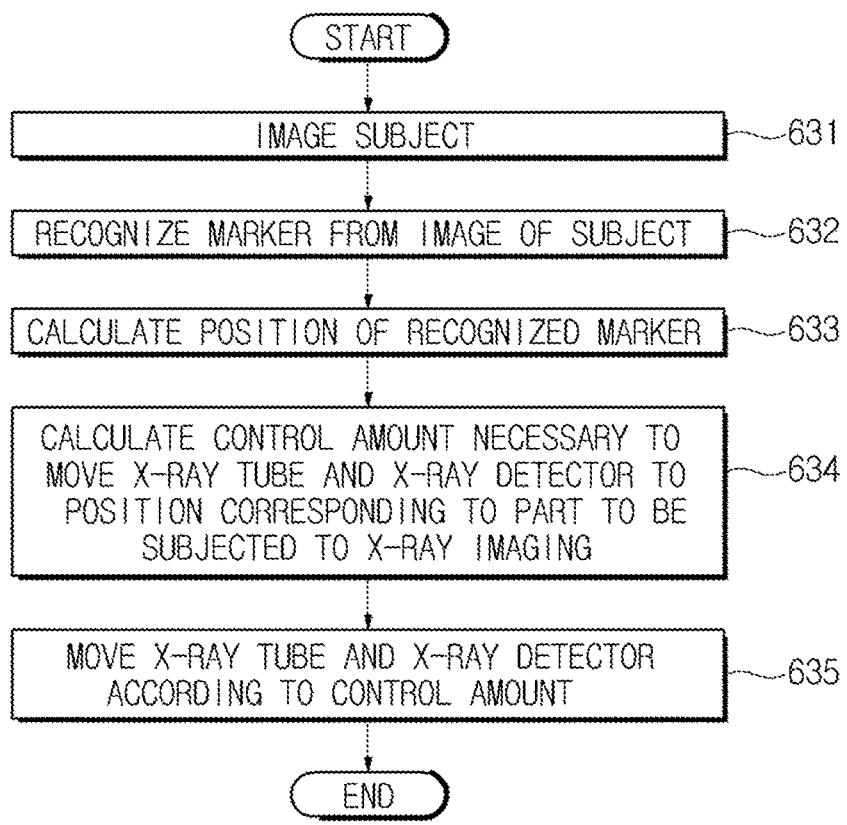
FIG. 18 is a flowchart which illustrates a method for controlling an X-ray imaging apparatus which corresponds to the exemplary embodiment illustrated in FIG. 14.

FIG. 18 is a flowchart which illustrates a method for controlling an X-ray imaging apparatus which corresponds to the exemplary embodiment illustrated in FIG. 14. The X-ray imaging apparatus applied to the present exemplary embodiment is a computed tomography (CT) device.

Referring to FIG. 18, in operation 631, a subject is imaged by using a camera before commencement of X-ray imaging. The subject is imaged in a state in which preparation for X-ray imaging is completed; in particular, in a state in which the subject is located on the slider of the patient table. A user locates a marker at a part to be subjected to X-ray imaging. The subject may be imaged in a single stage if the camera is a wide-angle camera which is capable of covering an entirety of the subject or the patient table, and may be imaged in multiple stages if the camera is a normal camera which has a normal lens mounted therein.

In operation 632, the marker is recognized from the image of the subject. The marker may be recognized by using at least one of various object recognition algorithms, and information relating to at least one of particular features of the marker may be pre-stored, and the marker which has the particular features may be recognized from the image of the subject.

In operation 633, the position of the recognized marker is calculated. More specifically, the position of the marker is calculated with respect to the slider of the patient table. If the position of the marker appearing in the subject image is calculated as two-dimensional coordinates on the slider, the position of the marker may indicate which point of the slider is located between the X-ray tube and the X-ray detector. For example, if the position of the marker is expressed as (m, n), the position (m, n) of the slider is located between the X-ray tube and the X-ray detector for X-ray imaging.

In operation 634, a control amount for causing the slider of the patient table to be moved to the position where the marker corresponds to the X-ray tube is calculated. Information relating to the relative position between the slider and the X-ray tube may be pre-stored. In particular, the actual position of the X-ray tube as expressed with respect to the coordinate system of the subject image may be pre-stored. A control amount for causing the position of the marker to correspond to the center of the radiation region of the X-ray tube on the slider is calculated based on the stored relative position information. Because the X-ray imaging apparatus according to the present exemplary embodiment is mounted in the gantry in a state in which the X-ray tube and the X-ray detector face each other, the position of the slider may correspond to any one of the X-ray tube and the X-ray detector.

In operation 635, the slider is moved based on the calculated control amount, and X-ray imaging is performed.

Figure 19:
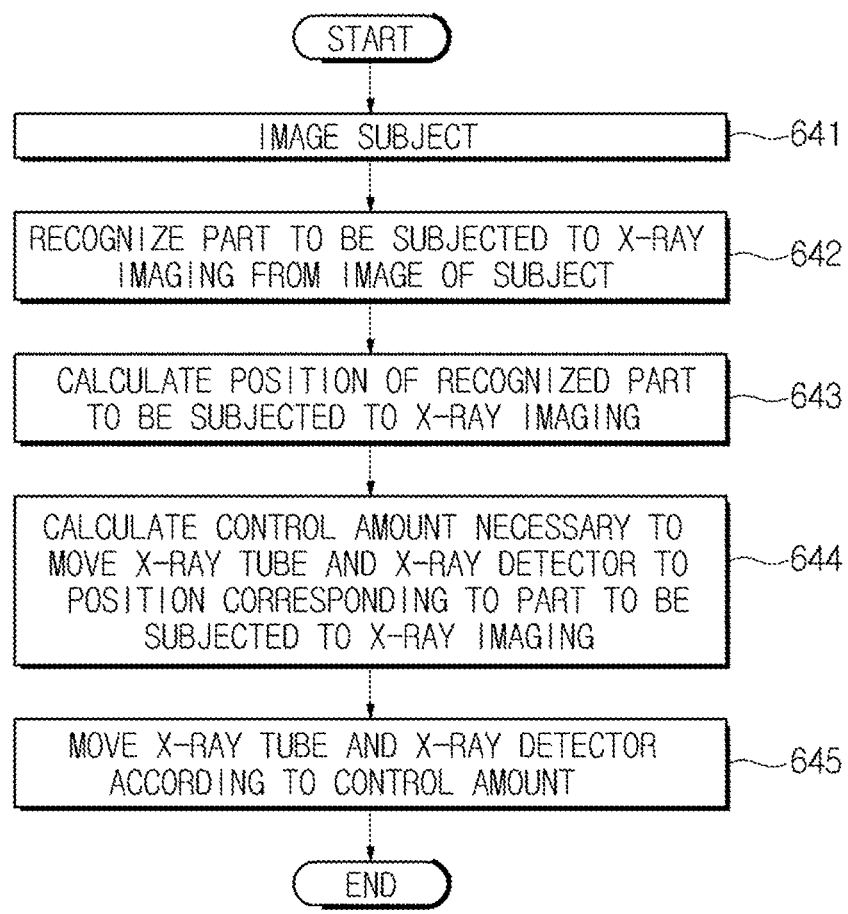
FIG. 19 is a flowchart which illustrates a method for controlling an X-ray imaging apparatus which corresponds to the exemplary embodiment illustrated in FIG. 15.

FIG. 19 is a flowchart which illustrates a method for controlling an X-ray imaging apparatus which corresponds to the exemplary embodiment illustrated in FIG. 15. The X-ray imaging apparatus applied to the present exemplary embodiment is a CT device.

Referring to FIG. 19, in operation 641, a subject is imaged by using a camera before commencement of X-ray imaging. The subject is imaged in a state in which preparation for X-ray imaging is completed; in particular, in a state in which the subject is located between the X-ray tube and the X-ray detector. The subject may be imaged in a single stage if the camera is a wide-angle camera which is capable of covering an entirety of the subject or the patient table, and may be imaged in multiple stages if the camera is a normal camera which has a normal lens mounted therein.

In operation 642, a part to be subjected to X-ray imaging is recognized from the image of the subject. The part to be subjected to X-ray imaging may be recognized by using at least one of various object recognition algorithms, and information relating to at least one of particular features of the part to be subjected to X-ray imaging may be pre-stored, and the part to be subjected to X-ray imaging which has the particular features may be recognized from the image of the subject.

In operation 643, the position of the recognized part to be subjected to X-ray imaging is calculated. In an exemplary embodiment, the position of the part to be subjected to X-ray imaging may be calculated on the slider. If the position of the part to be subjected to X-ray imaging may be calculated as two-dimensional coordinates, the position of the part to be subjected to X-ray imaging may indicate the center of the part to be subjected to X-ray imaging. However, the position of the center of the part to be subjected to X-ray imaging is not necessarily calculated, and the position of an arbitrary portion of the part to be subjected to X-ray imaging may be calculated based on the size of the part to be subjected to X-ray imaging.

In operation 644, a control amount for causing the slider of the patient table to be moved to a position where the part to be subjected to X-ray imaging corresponds to the X-ray tube is calculated. Information relating to the relative position between the slider and the X-ray tube may be pre-stored. A control amount for causing the position of the part to be subjected to X-ray imaging on the slider to correspond to the center of the radiation region of the X-ray tube is calculated based on the stored relative position information. Because the X-ray imaging apparatus according to the present exemplary embodiment is mounted in the gantry in a state in which the X-ray tube and the X-ray detector face each other, the position of the slider may correspond to any one of the X-ray tube and the X-ray detector.

In operation 645, the slider is moved based on the calculated control amount, and X-ray imaging is performed.

According to exemplary embodiments, it is possible to recognize a marker located at a part to be subjected to X-ray imaging from an image of a subject which is generated by using a camera, and to control a respective movement of each of an X-ray tube and an X-ray detector to a respective position which corresponds to the recognized marker in order to prevent inconvenience, such as a direct movement of the X-ray tube and the X-ray detector, and to reduce an X-ray imaging time and the amount of X-rays to which a patient is exposed.

Although a few exemplary embodiments have been shown and described, it would be appreciated by those skilled in the art that changes may be made in these exemplary embodiments without departing from the principles and spirit of the present inventive concept, the scope of which is defined in the claims and their equivalents.

The invention claimed is:

1. An X-ray imaging apparatus comprising:
   an X-ray tube which radiates X-rays toward a subject;
   an X-ray detector which detects X-rays which propagate through the subject;
   an imaging unit which generates an image of the subject;
   a recognizer which recognizes a part to be subjected to X-ray imaging from the generated image of the subject; and
   a position controller which controls a respective movement of each of the X-ray tube and the X-ray detector to a respective position which corresponds to the part to be subjected to X-ray imaging,
   wherein the recognizer comprises a marker recognizer which recognizes a marker from the generated image of the subject in order to recognize the part to be subjected to X-ray imaging of the subject, and the marker is located directly on the part of the subject that is to be subjected to X-ray imaging of the subject.

2. The X-ray imaging apparatus according to claim 1, wherein the position controller controls each of a center of an X-ray radiation region of the X-ray tube and a center of an X-ray detection region of the X-ray detector to match with a position of the marker.

3. The X-ray imaging apparatus according to claim 2, wherein the position controller comprises:
   a position calculator which calculates the position of the marker; and
   a control amount calculator which pre-stores information relating to a relative position between the generated image of the subject and at least one of the X-ray tube and the X-ray detector, and which calculates a control amount for causing respective positions of each of the X-ray tube and the X-ray detector to respectively correspond to the calculated position of the marker based on the relative position.

4. The X-ray imaging apparatus according to claim 1, wherein the marker recognizer recognizes at least one of a shape, a color, a material and a size of the marker.

5. The X-ray imaging apparatus according to claim 4, wherein the marker comprises an object having a recognizable feature and comprises a user's hand having a specific shape.

6. The X-ray imaging apparatus according to claim 4, wherein the marker recognizer recognizes an object having the at least one of the shape, the color, the material, and the size of the marker from the generated image of the subject.

7. The X-ray imaging apparatus according to claim 1, wherein the imaging unit comprises a wide-angle camera having an angle of view such that the image of the subject is generated in a single stage.

8. The X-ray imaging apparatus according to claim 3, wherein:
   the imaging unit is mounted in the X-ray tube, and
   the position calculator updates a position calculation result of the part to be subjected to X-ray imaging while the X-ray tube moves to the respective position which corresponds to the part to be subjected X-ray imaging.

9. An X-ray imaging apparatus comprising:
   a gantry which comprises an X-ray tube which radiates X-rays toward a subject and an X-ray detector which detects X-rays which propagate through the subject;
   a slider which moves the subject to a bore of the gantry;
   an imaging unit which generates an image of the subject;
   a recognizer which recognizes a part to be subjected to X-ray imaging from the generated image of the subject; and
   a position controller which controls a movement of the slider such that a position of the part to be subjected to X-ray imaging corresponds to a respective position of at least one of the X-ray tube and the X-ray detector,
   wherein the recognizer comprises a marker recognizer which recognizes a marker from the generated image of the subject in order to recognize the part to be subjected to X-ray imaging of the subject, and the marker is located directly on the part of the subject that is to be subjected to X-ray imaging of the subject.

10. The X-ray imaging apparatus according to claim 9, wherein the position controller comprises:
    a position calculator which calculates a position of the marker; and
    a control amount calculator which pre-stores information relating to a relative position between the generated image of the subject and at least one of the X-ray tube and the X-ray detector, and which calculates a control amount for causing the slider to move based on the pre-stored information relating to the relative position.

11. A method for controlling an X-ray imaging apparatus which comprises an X-ray tube which radiates X-rays toward a subject and an X-ray detector which detects X-rays which propagate through the subject, the method comprising:
    generating an image of the subject;
    recognizing a part to be subjected to X-ray imaging from the generated image of the subject; and
    controlling a respective movement of each of the X-ray tube and the X-ray detector to a respective position which corresponds to the part to be subjected to X-ray imaging,
    wherein the recognizing the part to be subjected to X-ray imaging comprises recognizing a marker from the generated image of the subject, the marker being located directly on the part of the subject that is to be subjected to X-ray imaging of the subject.

12. The method according to claim 11, wherein the controlling the respective movement of each of the X-ray tube and the X-ray detector to the position which corresponds to the part to be subjected to X-ray imaging comprises controlling each of a center of an X-ray radiation region of the X-ray tube and a center of an X-ray detection region of the X-ray detector to match with a position of the marker.

13. The method according to claim 11, wherein the controlling the respective movement of each of the X-ray tube and the X-ray detector to the position which corresponds to the part to be subjected to X-ray imaging comprises pre-storing information relating to a relative position between the generated image of the subject and at least one of the X-ray tube and the X-ray detector, calculating a position of the marker, and calculating a control amount for causing respective positions of each of the X-ray tube and the X-ray detector to respectively correspond to the calculated position of the marker based on the relative position.

14. The method according to claim 11, further comprising pre-storing information relating to a feature which comprises information relating to at least one of a shape, a color, a material and a size of the marker.

15. The method according to claim 14, wherein the marker comprises an object having a recognizable feature and comprises a user's hand having a specific shape.

16. The method according to claim 14, wherein the recognizing the part to be subjected to X-ray imaging of the subject comprises recognizing an object having the feature which comprises the information relating to at least one of the shape, the color, the material, and the size of the marker from the generated image of the subject.

17. The method according to claim 13, wherein the image of the subject is generated by using a wide-angle camera having an angle of view such that the image of the subject is generated in a single stage.

18. The method according to claim 17, wherein:
an imaging unit is mounted in the X-ray tube, and
the calculating the position of the marker comprises updating a position calculation result of the part to be subjected to X-ray imaging while the X-ray tube moves to the respective position which corresponds to the part to be subjected X-ray imaging.

19. A method for controlling an X-ray imaging apparatus which comprises a gantry which comprises an X-ray tube which radiates X-rays toward a subject and an X-ray detector which detects X-rays which propagate through the subject, the method comprising:
moving a slider, on which the subject is located, to a bore of the gantry;
generating an image of the subject;
recognizing a part to be subjected to X-ray imaging from the generated image of the subject; and
controlling a movement of the slider such that the part to be subjected to X-ray imaging corresponds to a respective position of at least one of the X-ray tube and the X-ray detector,
wherein the recognizing the part to be subjected to X-ray imaging comprises recognizing a marker from the generated image of the subject, the marker being located directly on the part of the subject that is to be subjected to X-ray imaging of the subject.

20. The method according to claim 19, wherein the controlling the movement of the slider comprises pre-storing information relating to a relative position between the generated image of the subject and at least one of the X-ray tube and the X-ray detector and calculating a control amount for causing the slider to move based on the pre-stored information relating to the relative position.

21. The method according to claim 20, wherein the calculating the control amount for causing the slider to move comprises calculating a control amount for causing the slider to move such that a position of the marker corresponds to at least one of the X-ray tube and the X-ray detector.

22. The X-ray imaging apparatus according to claim 1, wherein the imaging unit comprises a camera having a wide-angle lens which covers an entirety of a patient table in a single stage.

23. An X-ray imaging apparatus comprising:
an X-ray tube configured to radiate X-rays toward a subject;
an X-ray detector configured to detect X-rays which propagate through the subject;
an image generator configured to generate an image of the subject; and
a controller configured to recognize a part to be subjected to X-ray imaging from the generated image of the subject by using a marker which is located directly on the part of the subject that is to be subjected to X-ray imaging of the subject, and to control a respective movement of each of the X-ray tube and the X-ray detector to a respective position which corresponds to the part to be subjected to X-ray imaging.

24. The X-ray imaging apparatus according to claim 23, wherein the controller is further configured to recognize at least one of a shape, a color, a material and a size of the marker.

25. The X-ray imaging apparatus according to claim 24, wherein the marker comprises an object having a recognizable feature and comprises a user's hand having a specific shape.

26. The X-ray imaging apparatus according to claim 24, wherein the controller is further configured to recognize an object having the at least one of the shape, the color, the material, and the size of the marker from the generated image of the subject.

27. The X-ray imaging apparatus according to claim 23, wherein the image generator comprises a wide-angle camera having an angle of view such that the image of the subject is generated in a single stage.

28. A method for controlling an X-ray imaging apparatus which comprises an X-ray tube which radiates X-rays toward a subject and an X-ray detector which detects X-rays which propagate through the subject, the method comprising:
generating an image of the subject;
recognizing a part to be subjected to X-ray imaging from the generated image of the subject by using a marker which is located directly on the part of the subject that is to be subjected to X-ray imaging of the subject; and
controlling a respective movement of each of the X-ray tube and the X-ray detector to a respective position which corresponds to the part to be subjected to X-ray imaging.

29. The method according to claim 28, further comprising pre-storing information relating to a feature which comprises information relating to at least one of a shape, a color, a material and a size of the marker.

30. The method according to claim 29, wherein the marker comprises an object having a recognizable feature and comprises a user's hand having a specific shape.

31. The method according to claim 29, wherein the recognizing the part to be subjected to X-ray imaging of the subject comprises recognizing an object having the feature which comprises the information relating to at least one of the shape, the color, the material, and the size of the marker from the generated image of the subject.

32. The method according to claim 28, wherein the image of the subject is generated by using a wide-angle camera having an angle of view such that the image of the subject is generated in a single stage.

\* \* \* \* \*